United States Patent [19]

Takematsu et al.

[11] 4,233,061
[45] Nov. 11, 1980

[54] NOVEL BENZENESULFONAMIDE DERIVATIVES

[75] Inventors: Tetsuo Takematsu; Makoto Konnai; Hiroyoshi Omokawa, all of Utsunomiya, Japan

[73] Assignee: Utsunomiya University, Tochigi, Japan

[21] Appl. No.: 974,517

[22] Filed: Dec. 29, 1978

Related U.S. Application Data

[62] Division of Ser. No. 837,911, Sep. 29, 1977, Pat. No. 4,157,257.

[30] Foreign Application Priority Data

Oct. 1, 1976 [JP] Japan .................. 51/118343
May 20, 1977 [JP] Japan .................. 52/58369
Aug. 2, 1977 [JP] Japan .................. 52/92803

[51] Int. Cl.² ................................. A01N 9/14
[52] U.S. Cl. ........................... 71/103; 564/89; 564/92
[58] Field of Search ............... 71/103; 260/556 AR

[56] References Cited

U.S. PATENT DOCUMENTS

| | | | |
|---|---|---|---|
| 2,927,126 | 3/1960 | Pursglove | 71/103 |
| 3,246,974 | 4/1966 | Brokke et al. | 71/103 |
| 3,246,976 | 4/1966 | Brokke et al. | 71/103 |
| 3,342,859 | 9/1967 | Dorfman et al. | 71/118 |
| 3,498,781 | 3/1970 | Buntin | 71/118 |
| 3,640,699 | 2/1972 | Horrom et al. | 71/118 |
| 3,752,661 | 8/1973 | Orlett | 71/103 |
| 3,888,897 | 6/1975 | Martin | 71/103 |
| 3,979,203 | 9/1976 | Bullock et al. | 71/103 |
| 4,082,799 | 4/1978 | Baker et al. | 71/118 |
| 4,113,463 | 9/1978 | Oshio et al. | 71/103 |

*Primary Examiner*—Glennon H. Hollrah
*Attorney, Agent, or Firm*—Wenderoth, Lind & Ponack

[57] ABSTRACT

A compound of the general formula

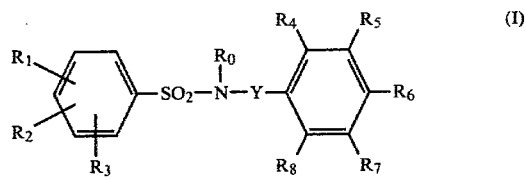

wherein $R_0$ represents an alkyl group optionally having a substituent selected from the class consisting of a cyano group, lower alkoxy groups and di-(lower alkyl)amino groups, a lower alkenyl group, or a lower alkynyl group; $R_1$, $R_2$ and $R_3$, independently from each other, represent a hydrogen atom, a halogen atom, a lower alkyl group, or a lower alkoxy group; $R_4$, $R_5$, $R_6$, $R_7$ and $R_8$, independently from each other, represent a hydrogen atom, a halogen atom, a lower alkyl group, or a lower alkoxy group; Y represents a group of the formula

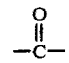

or a group of the formula

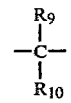

in which one of $R_9$ and $R_{10}$ is a lower alkyl group and the other is a hydrogen atom or a lower alkyl group; with the proviso that when Y is the group

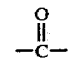

and $R_0$ represents an unsubstituted alkyl group, $R_4$, $R_5$, $R_6$, $R_7$ and $R_8$ do not represent hydrogen atoms at the same time. The compounds of formula (I) are produced by the reaction of the corresponding benzenesulfonamide derivatives with the corresponding benzyl or benzoyl halides; the reaction of the corresponding benzenesulfonyl halides with the corresponding benzylamines or benzoyl amides; or by the alkylation, alkenylation or alkynylation of the corresponding compounds of formula (I) in which $R_0$ is hydrogen. The compounds of formula (I) have superior selective herbicidal effects, and are useful as active ingredients of herbicides, especially those for application to aquatic rice paddies.

24 Claims, No Drawings

NOVEL BENZENESULFONAMIDE DERIVATIVES

This is a division of application Ser. No. 837,911, filed Sept. 29, 1977, now U.S. Pat. No. 4,157,257.

This invention relates to novel benzenesulfonamide derivatives. More specifically, the invention relates to certain novel N,N-disubstituted benzenesulfonamide derivatives, a process for their preparation, and to their use as herbicides.

Numerous benzenesulfonamide derivatives have been known. For example, Swiss Pat. No. 224,856 discloses that N-methyl-N-benzoyl-3,4-dichlorobenzenesulfonamide is useful as an insecticide. U.S. Pat. No. 3,245,913 states that N-methyl-N-benzoyl-substituted benzenesulfonamides are effective as bleaching agents. Japanese Patent Publication No. 7216/74 suggests the utilization of N-methyl-N-benzoyl-3,5-dibromo-6-acetoxybenzenesulfonamide as a herbicide.

Elsewhere, Zh. Org. Chim., 7, 363 (1971) reports N-halogenated ethyl-N-substituted benzoyl-4-methyl-benzenesulfonamides as known compounds, and Ukrain. Khim. Zhur., 26, 496 (1960) reports N-isopropyl-N-benzoyl-p-chlorobenzenesulfonamide as a known compound.

It has now been found in accordance with this invention that a certain group of novel N,N-disubstituted benzenesulfonamide derivatives are useful as herbicides, and have superior selective herbicidal activity against the emergence of barnyard grasses (especially, *Echinochloa crusgalli* Beauv.) without substantially affecting rice plants. This is surprising in view of the fact that since barnyard grass, the most hazardous weed in a paddy field, is a graminaceous grass, it has been considered as impossible to selectively control barnyard grass without causing phytotoxicity to rice.

An object of this invention is to provide novel N,N-disubstituted benzenesulfonamide derivatives having superior selective herbicidal activity.

Another object of this invention is to provide a process for preparing these novel N,N-disubstituted benzenesulfonamide derivatives.

Still another object of this invention is to provide herbicides having superior selective herbicidal activity which can strongly control various weeds, especially barnyard grasses, without substantially causing phytotoxicity to agricultural crops, especially rice plant in a paddy field.

Yet another object of this invention is to provide a method for selectively controlling weeds in agricultural crops without substantially affecting the crops.

Other objects and advantages of this invention will become more apparent from the following detailed description.

The present invention provides a compound of the general formula

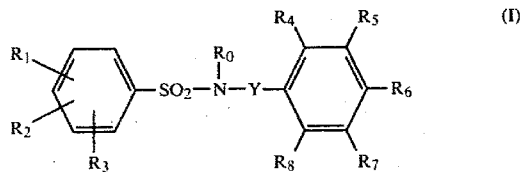

wherein $R_0$ represents an alkyl group optionally having a substituent selected from the class consisting of a cyano group, lower alkoxy groups and di-(lower alkyl)amino groups, a lower alkenyl group, or a lower alkynyl group; $R_1$, $R_2$ and $R_3$, independently from each other, represent a hydrogen atom, a halogen atom, a lower alkyl group, or a lower alkoxy group; $R_4$, $R_5$, $R_6$, $R_7$ and $R_8$, independently from each other, represent a hydrogen atom, a halogen atom, a lower alkyl group, or a lower alkoxy group; Y represents a group of the formula

or a group of the formula

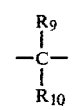

in which one of $R_9$ and $R_{10}$ is a lower alkyl group and the other is a hydrogen atom or a lower alkyl group; with the proviso that when Y is the group

and $R_0$ represents an unsubstituted alkyl group, $R_4$, $R_5$, $R_6$, $R_7$ and $R_8$ do not represent hydrogen atoms at the same time.

In the present specification and the appended claims, the term "lower" means that a group or radical modified by this term contains up to 6, preferably 1 to 4, carbon atoms.

The term "alkyl group", as used in the present specification and the appended claims, denotes a saturated aliphatic hydrocarbon group which may be of straight chain or branched chain, and contain generally up to 20, preferably up to 15, more preferably up to 12, carbon atoms. Examples of the alkyl group include methyl, ethyl, n- or iso-propyl, n-, iso-, sec- or tert-butyl, n- or neo-pentyl, n-hexyl, n-heptyl, n-octyl, n-nonyl, n-decyl, n-undecyl, and n-dodecyl. Where $R_0$ in formula (I) represents an alkyl group, the alkyl group may contain a substituent. The substituent is selected from the class consisting of a cyano group (CN), lower alkoxy groups such as a methoxy or ethoxy group, and di(lower alkyl)amino groups such as a dimethylamino or diethylamino group. When any of $R_1$ to $R_8$ represents a lower alkyl, it is desirably a methyl or ethyl group.

The term "lower alkenyl group" denotes a lower aliphatic hydrocarbon group which contains one carbon-to-carbon double bond, and may be of straight chain or branched chain. Examples are vinyl, allyl and butenyl groups, the allyl group being most preferred.

The term "lower alkynyl group" denotes a lower aliphatic hydrocarbon group containing one carbon-to-carbon triple bond. A propargyl group is a typical example of the lower alkynyl group.

The term "lower alkoxy group" means a lower alkyl ether group and includes, for example, methoxy, ethoxy, n- or iso-propoxy, n-, iso-, sec- or tert-butoxy. Of these, methoxy and ethoxy groups are preferred.

The term "halogen atom" denotes fluorine, chlorine, bromine and iodine atoms. Of these, a chlorine atom is most preferred, and next comes a fluorine atom.

Thus, preferred substituents $R_0$ are alkyl groups containing up to 15 carbon atoms which may contain a substituent selected from the class consisting of a cyano group, lower alkoxy groups and di-(lower alkyl)amino groups; a lower alkenyl group; or a propargyl group. Of these, the lower alkenyl groups, above all, an allyl group, and the propargyl group are especially preferred.

Preferred species of $R_1$, $R_2$ and $R_3$ are a hydrogen atom, a halogen atom, a methyl group, an ethyl group, a methoxy group, and an ethoxy group. Preferably, a least one of $R_1$, $R_2$ and $R_3$ is a hydrogen atom, and moreover, at least one of these groups is desirably located at the 4-position of the benzene ring to which they are bonded.

Preferred atoms or groups represented by $R_4$, $R_5$, $R_6$, $R_7$ and $R_8$ are a hydrogen atom, a halogen atom, a methyl group, an ethyl group, a methoxy group, and an ethoxy group, the hydrogen atom or halogen atom being especially preferred. When at least one of $R_4$ to $R_8$ represent the aforesaid groups other than hydrogen, one or two of them are desirably located at the 2-position and/or the 4-position on the benzene ring. When Y is a carbonyl group

it is most preferred that at least one, preferably one or two, of groups $R_4$ to $R_8$ be halogen and the remainder be hydrogen. If Y is a a substituted methylene group

it is most convenient that all of groups $R_4$ to $R_8$ be hydrogen atoms at the same time.

Of the compounds of formula (I), a group of preferred compounds are those expressed by the formula

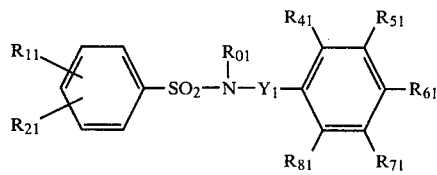
(I-a)

wherein $R_{01}$ represents an alkyl group containing up to 15 carbon atoms which may contain a substituent selected from the class consisting of a cyano group, lower alkoxy groups and di-(lower alkyl)amino groups, a lower alkenyl group, or a propargyl group; $R_{11}$ and $R_{21}$, independently from each other, represent a hydrogen atom, a halogen atom, a methyl group, an ethyl group, or a methoxy group; $R_{41}$, $R_{51}$, $R_{61}$, $R_{71}$ and $R_{81}$, independently from each other, represent a hydrogen atom, a halogen atom, a methyl group or a methoxy group; $Y_1$ represents the group

or

in which one of $R_{91}$ and $R_{101}$ is a methyl or ethyl group, and the other is a hydrogen atom or a methyl or ethyl group; with the proviso that when $Y_1$ is the group CO and $R_{01}$ is an unsubstituted alkyl group, $R_{41}$, $R_{51}$, $R_{61}$, $R_{71}$ and $R_{81}$ do not represent hydrogen atoms at the same time.

A group of more preferred compounds of formula (I-a) are those in which $R_{01}$ represents an allyl group or a propargyl group and $Y_1$ represents the group

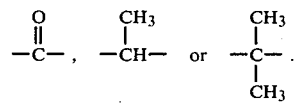

A combination of the group

as $Y_1$ and an allyl or propargyl group as $R_{01}$ and a combination of

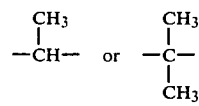

as $Y_1$ and an allyl group as $R_{01}$ are especially advantageous.

Thus, a group of especially preferred compounds of formula (I-a) are those in which $R_{01}$ represents an allyl or propargyl group; $Y_1$ represents the group

$R_{41}$ is a halogen atom; and any one of $R_{51}$, $R_{61}$, $R_{71}$ and $R_{81}$, especially $R_{61}$, is a hydrogen or halogen atom and the rest are hydrogen atoms. In this case, it is desirable that $R_{11}$ and $R_{21}$, independently from each other, represent a hydrogen atom or a methyl group, especially hydrogen.

Another group of especially preferred compounds of formula (I-a) are those in which $R_{01}$ is an allyl group, $Y_1$ is the group

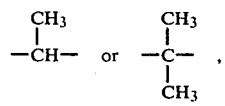

$R_{11}$ represents a hydrogen atom, a halogen atom, or a methyl or methoxy group, $R_{21}$ is a hydrogen atom, $R_{41}$ and $R_{61}$, independently from each other, represent a hydrogen atom, a halogen atom or a methyl group, and $R_{51}$, $R_{71}$ and $R_{81}$ are all hydrogen atoms.

As will be described in detail hereinbelow, the compounds of formula (I) provided by this invention have superior selective herbicidal activity. From the view-point of herbicidal activity, most preferred among the compounds of formula (I) are those of the following formula

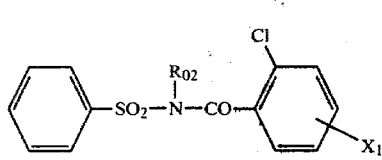  (I-b)

ps wherein $R_{02}$ is an allyl or propargyl group, and $X_1$ is a hydrogen or chlorine atom; and those of the following formula

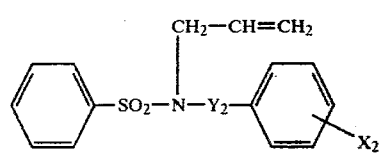  (I-c)

wherein $Y_2$ is the group

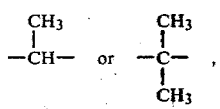

and $X_2$ is a hydrogen or chlorine atom.

Typical examples of the compounds of formula (I) provided by the present invention except those specifically shown in Examples to be given hereinbelow are listed below.

N-allyl-N-(4-chlorobenzoyl)benzenesulfonamide,
N-allyl-N-(3,4-dichlorobenzoyl)benzenesulfonamide,
N-allyl-N-(2,5-dichlorobenzoyl)benzenesulfonamide,
N-allyl-N-(3,5-dichlorobenzoyl)benzenesulfonamide,
N-allyl-N-(pentachlorobenzoyl)benzenesulfonamide, and
N-allyl-N-benzoylbenzenesulfonamide.

Specific examples of the most preferred compounds in the present invention are:
N-allyl-N-(2-chlorobenzoyl)benzenesulfonamide,
N-allyl-N-(2,4-dichlorobenzoyl)benzenesulfonamide,
N-propargyl-N-(2-chlorobenzoyl)benzenesulfonamide,
N-allyl-N-(α,α-dimethylbenzyl)benzenesulfonamide,
N-allyl-N-(α-methylbenzyl)benzenesulfonamide,
N-allyl-N-(α-methyl-4-chlorobenzyl)benzenesulfonamide, and
N-allyl-N-(α,α-dimethyl-4-chlorobenzyl)benzenesulfonamide.

According to the present invention, the compound of formula (I) can be produced by
(a) reacting a benzenesulfonamide derivative of the general formula

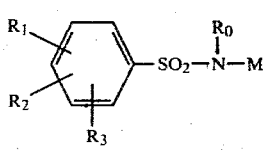  (II)

wherein M represents a hydrogen atom or an alkali metal atom, and $R_0$, $R_1$, $R_2$ and $R_3$ are as defined hereinabove, with a compound of the general formula

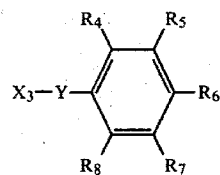  (III)

wherein
$X_3$ is a halogen atom, and $R_4$, $R_5$, $R_6$, $R_7$,
$R_8$ and Y are as defined hereinabove,
or (b) reacting a benzenesulfonyl halide of the general formula

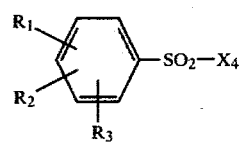  (IV)

wherein $X_4$ is a halogen atom, and $R_1$, $R_2$ and $R_3$ are as defined hereinabove, with a compound of the general formula

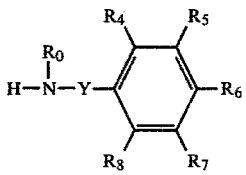  (V)

wherein $R_0$, $R_4$, $R_5$, $R_6$, $R_7$, $R_8$ and Y are as defined hereinabove, or (c) reacting a compound of the general formula

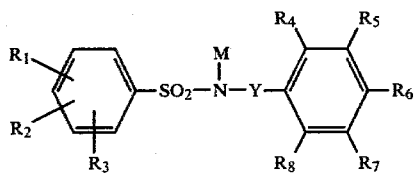  (VI)

wherein
$R_1$, $R_2$, $R_3$, $R_4$, $R_5$, $R_6$, $R_7$, $R_8$, Y and
M are as defined hereinabove, with a compound of the formula $R_0—X_4$  (VII)

wherein $X_4$ is a halogen atom, and $R_0$ is as defined above.

The reaction of the benzenesulfonamide derivative of formula (II) with the compound of formula (III) in method (a) may be carried out in the absence of a solvent. Generally, however, it is preferably carried out in an inert solvent. Examples of usable solvents are water, ethers such as diethyl ether, dioxane or tetrahydrofuran, aromatic hydrocarbons such as benzene, toluene or xylene, N,N-dimethyl formamide, dimethyl sulfoxide, and pyridine. For certain types of the starting materials, alcohols such as methanol or ethanol, ketones such as acetone or methyl ethyl ketone, or halogenated hydrocarbons such as methylene chloride, chloroform or carbon tetrachloride may also be used as the solvents.

These solvents are used singly or as mixtures of two or more.

The reaction temperature is not critical, and can be varied over a wide range according, for example, to the types of the starting materials, and the type of the solvent. Advantageously, the reaction temperature is generally from about 0° C. to the reflux temperature of the reaction mixture, preferably from room temperature to the reflux temperature of the reaction mixture. It is sufficient that the reaction pressure is atmospheric pressure, but if desired, reduced or elevated pressures may be employed. Under these conditions, the reaction can be terminated in about 0.5 to 5 hours.

The ratio between the compound of formula (II) and the compound of formula (III) to be reacted is not critical, and can be varied over a wide range. Advantageously, the compound of formula (III) is used in an amount of generally at least 1 mole, preferably 1.1 to 2 moles, per mole of the compound of formula (II).

If a compound of formula (II) in which M is a hydrogen atom is used as the starting material, the above reaction is advantageously carried out in the presence of an acid binder. Examples of usable acid binders are basic substances, for example alkali metal hydroxides such as sodium hydroxide or potassium hydroxide, and organic bases such as pyridine or triethylamine.

Examples of preferred alkali metal atoms for M in formula (II) are lithium, potassium and sodium. A compound of formula (II) in which M is an alkali metal atom may be prepared in advance from a compound of formula (II) in which M is a hydrogen atom and an alkali metal hydride such as sodium hydride or potassium hydride or an alkali metal such as sodium or potassium, and then reacted with the compound of formula (III). Or it may be formed in situ by causing the alkali metal hydride or alkali metal to be present in the reaction system.

Thus, in the reaction between the compound of formula (II) and the compound of formula (III), the use of a reaction medium comprising a combination of sodium hydroxide or potassium hydroxide and water; a combination of pyridine and an ether or an aromatic hydrocarbon; or a combination of an alkali metal hydride and N,N-dimethyl formamide or dimethyl sulfoxide is advantageous.

The amount of each of the alkali metal hydroxide, organic base, alkali metal hydride, etc. may be at least 1 mole, preferably 1.1 to 3 moles, per mole of the compound of formula (II).

In the compound of formula (III), a chlorine atom is especially preferred as the halogen atom represented by $X_3$.

The method (a) can be especially advantageously applied to the production of compounds of formula (I) in which Y represents

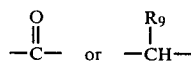

such as

The resulting reaction mixture containing the compound of formula (I) can be recovered by a known procedure. For example, water is added to the reaction mixture, and when the final product precipitates as a solid, it can be separated by filtration, centrifugal separation or the like. When the final product precipitates as an oil, it can be separated by solvent extraction, decantation or the like. In the case of solvent extraction, benzene, ethyl acetate, and chloroform may be suitably used as solvents. The crude final product separated can be purified, as needed, by recrystallization, distillation, chromatography, etc.

According to method (b) in accordance with this invention, the benzenesulfonyl halide of formula (IV) is reacted with the amine of formula (V). This reaction can be performed in the absence of a solvent, but usually, it is preferred to carry it out in an inert solvent. Examples of useful inert solvents are water, aromatic hydrocarbons such as benzene, toluene or xylene, ethers such as diethyl ether, tetrahydrofuran or dioxane, ketones such as acetone or methyl ethyl ketone, and halogenated hydrocarbons such as methylene chloride, chloroform or carbon tetrachloride. Water, benzene, and tetrahydrofuran are especially preferred.

The reaction temperature is not critical, and can be varied over a wide range according, for example, to the types of the starting materials and/or the type of the solvent used. It is advantageous that the reaction temperature is generally from about 0° C. to the reflux temperature of the reaction mixture, preferably from room temperature to about 80° C. The reaction pressure is usually atmospheric pressure, but if desired, elevated or reduced pressures may be employed.

If desired, the reaction in method (b) may be carried out in the presence of a catalyst. Useful catalysts are, for example, alkali metal hydroxides such as sodium hydroxide, and organic bases such as pyridine or triethylamine. The amount of the catalyst is advantageously about 1 to 2 moles per mole of the compound of formula (IV).

The ratio between the compound of formula (IV) and the compound of formula (V) is not critical and can be varied over a wide range. Generally, it is advantageous that the compound of formula (IV) is used in an amount of at least 1 mole, preferably 1.1 to 2 moles, per mole of the compound of formula (V).

Under the reaction conditions described hereinabove, the reaction is generally terminated in about 1 to 6 hours. The separation of the final product from the reaction mixture and its purification can be performed in the same manner as mentioned hereinabove with regard to method (a).

In method (c) of this invention, the compound of formula (VI) is treated with an alkylating, alkenylating or alkynylating agent [the compound of formula (VIII)] to introduce the group $R_0$ into the N-atom of the compound of formula (VI).

Examples of the compound of formula (VII) include alkyl halides such as methyl bromide, ethyl chloride, methyl iodide, n-butyl iodide and n-decyl bromide, substituted alkyl halides such as cyanomethyl bromide, methoxypropyl iodide and dimethylaminopropyl bromide, alkenyl halides such as allyl chloride, and alkynyl halides such as propargyl chloride.

Preferably, the reaction between the compound of formula (VI) and the compound of formula (VII) is generally carried out in an inert solvent. Useful solvents include, for example, ethers such as diethyl ether, tetrahydrofuran or dioxane, aromatic hydrocarbons such as benzene, toluene or xylene, alcohols such as methanol or ethanol, ketones such as acetone or methyl ethyl ketone, halogenated hydrocarbons such as methylene chloride or chloroform, N,N-dimethyl formamide, dimethyl sulfoxide, pyridine, and water.

Advantageously, the reaction of a compound of formula (VI) in which M is hydrogen with the compound of formula (VII) can be carried out in the presence of a basic catalyst, for example an alkali metal hydroxide such as sodium hydroxide or potassium hydroxide, an organic base such as pyridine or triethylamine, an alkali metal hydride such as sodium hydride or potassium hydride, or an alkali metal such as metallic sodium or potassium. The catalyst can be used in an amount of 1 to 2 moles per mole of the compound of formula (VI). A compound of formula (VI) in which M is an alkali metal atom can be prepared by the reaction of a compound of formula (VI) in which M is hydrogen with the alkali metal hydride or alkali metal. It may also be produced in situ in the reaction system.

The reaction temperature is not critical, and can be varied widely according, for example, to the types of the starting materials, or the type of the solvent. Generally, the reaction temperature is from about 0° C. to the reflux temperature of the reaction mixture, preferably from room temperature to the reflux temperature of the reaction mixture. Usually, the reaction pressure is atmospheric pressure, but if desired, reduced or elevated pressures may be used.

The ratio between the compound of formula (VI) and the compound of formula (VII) is not critical, and can be varied widely. The compound of formula (VII) is used in an amount of at least 1 mole, usually 1.2 to 3 moles, per mole of the compound of formula (VI).

Under the reaction conditions described hereinabove, the reaction can be terminated in about 1 to 10 hours. The final product of formula (I) can be obtained in good yields from the resulting reaction mixture in the same manner as described hereinabove.

Some of the compounds of formula (VI) used in method (c) in this invention, especially those in which Y

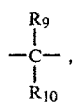

are novel compounds, and can be prepared, for example, by reacting correspondingly substituted benzylamines with the corresponding benzenesulfonyl halides in the presence of catalysts such as sodium hydroxide.

The production of the compound (I) of this invention is illustrated by the following Examples.

EXAMPLE 1

N-Methyl-N-($\alpha,\alpha$-dimethylbenzyl)benzenesulfonamide 27.5 g (0.1 mole) of N-($\alpha,\alpha$-dimethylbenzyl)benzenesulfonamide was added to 5.8 g (0.12 mole) of 50% sodium hydride in 200 ml of dry N,N-dimethyl formamide. The mixture was stirred at room temperature for 30 minutes to react them. To the resulting sodium salt of N-($\alpha,\alpha$-dimethylbenzyl)benzenesulfonamide was added 16.1 g (0.17 mole) of methyl bromide. The mixture was heated to 60° C. and stirred for 1 hours. The N,N-dimethyl formamide was distilled off under reduced pressure, and cold water was added. The resulting white solid was recrystallized from methanol to afford N-methyl-N-($\alpha,\alpha$-dimethylbenzyl)benzenesulfonamide in a yield of 87%. This compound is designated as compound No. 64 in Table 2 below, and its melting point and elemental analysis values are shown in Table 2.

The N-($\alpha,\alpha$-dimethylbenzyl)benzenesulfonamide used as a starting compound in the above procedure could be prepared in the following manner. A two-layered mixture consisting of 33.8 g (0.25 mole) of $\alpha,\alpha$-dimethylbenzylamine and 120 ml of a 10% aqueous solution of sodium hydroxide was stirred at below 40° C., and 44.1 g of benzenesulfonyl chloride was added dropwise. Stirring the mixture for an additional 1.5 hours afforded a white precipitate. The solid precipitate was collected by filtration, and recrystallized from methanol to afford N-($\alpha,\alpha$-dimethylbenzyl)benzenesulfonamide having melting point of 114° to 115° C. in a yield of 67%.

Starting compounds shown in Table 1 were prepared by the same procedure as above except that $\alpha$-methylbenzylamine or the correspondingly substituted $\alpha,\alpha$-dimethylbenzylamines were used instead of the $\alpha,\alpha$-dimethylbenzylamine, and the correspondingly substituted benzenesulfonyl chlorides were used instead of the benzenesulfonyl chloride.

TABLE 1

$$Q_1\text{-}Q_2\text{-C}_6\text{H}_3\text{-SO}_2\text{-NH-C}(CH_3)(Q_3)\text{-C}_6\text{H}_4\text{-}Q_4 \quad (VI\text{-}1)$$

| Compound No. | $Q_1$ | $Q_2$ | $Q_3$ | $Q_4$ | Melting point or refractive index |
|---|---|---|---|---|---|
| 2 | 2-CH$_3$ | H | CH$_3$ | H | 120–121° C. |
| 3 | 4-CH$_3$ | H | CH$_3$ | H | 135–137° C. |
| 4 | 4-CH$_3$O | H | CH$_3$ | H | 128–130° C. |
| 5 | 4-Cl | H | CH$_3$ | H | 125–126° C. |
| 6 | 2-CH$_3$ | 5-CH$_3$ | CH$_3$ | H | 112.0–112.5° C. |
| 7 | 4-C$_2$H$_5$ | H | CH$_3$ | H | 103.5–104.0° C. |
| 8 | H | H | CH$_3$ | 4-Cl | 105–107° C. |
| 9 | H | H | CH$_3$ | CH$_3$ | 72–78° C. |
| 10 | H | H | H | H | 102–103° C. |
| 11 | 4-CH$_3$ | H | H | H | 82–83.5° C. |
| 12 | 4-C$_2$H$_5$ | H | H | H | $n_D^{26} = 1.5656$ |
| 13 | 4-Cl | H | H | H | 74–75° C. |
| 14 | 2-CH$_3$ | 4-CH$_3$ | H | H | 104.5–105° C. |
| 15 | 2-CH$_3$ | 5-CH$_3$ | H | H | 72.5–73° C. |

Compounds Nos. 65 to 88 and 95 to 102 shown in Table 2 could be produced in the same way as in Example 1 using the starting compounds Nos. 2 to 15.

EXAMPLE 2

N-Allyl-N-($\alpha$-methyl-2-chlorobenzyl)benzenesulfonamide 1.97 g (0.01 mole) of N-allylbenzenesulfonamide was added to 0.58 g (0.012 mole) of 50% sodium hydride in 15 ml of dry N,N-dimethylformamide. The mixture was stirred at room temperature for 30 minutes to react them. To the resulting sodium salt was added 2.10 g (0.012 mole) of $\alpha$-methyl-2-chlorobenzyl chloride. The mixture was stirred at room temperature for 1 hour. The N,N-dimethyl formamide was distilled off under reduced pressure, and cold water was added. The resulting oil layer was extracted with benzene. The benzene layer was dried over anhydrous magnesium sulfate, concentrated, and purified by silica gel chromatography to afford the final product. The final product is designated as compound No. 89 in Table 2, and its melting point and elemental analysis values are shown in Table 2.

Compounds Nos. 90 to 94 shown in Table 2 could be prepared in the same way as in Example 2.

EXAMPLE 3

N-methyl-N-(2-chlorobenzoyl)benzenesulfonamide 1.71 g (0.01 mole) of N-methylbenzenesulfonamide was added to 0.58 g (0.012 mole) of 50% sodium hydride in 15 ml of dry N,N-dimethylformamide. The mixture was stirred at room temperature for 30 minutes to react them. To the resulting sodium salt was added 2.10 g (0.012 mole) of 2-chlorobenzoyl chloride, and the mixture was stirred at room temperature for 1 hour. The N,N-dimethyl formamide was distilled off under reduced pressure. Cold water was added, and the resulting oil layer was extracted with benzene. The benzene layer was dried over anhydrous magnesium sulfate, and concentrated to afford almost pure N-methyl-N-(2-chlorobenzoyl)benzenesulfonamide in a yield of 92%. For further purification, this compound was subjected to chromatography or high vacuum distillation. This compound is designated as compound No. 16 in Table 2, and its melting point and elemental analysis values are shown in Table 2.

Compounds Nos. 17 to 63 in Table 2 could be prepared in the same way as in Example 3.

EXAMPLE 4

N-Allyl-N-(2-chlorobenzoyl)benzenesulfonamide 3.0 g (0.01 mole) of N-2-chlorobenzoyl benzenesulfonamide prepared from benzenesulfonamide and 2-chlorobenzoyl chloride was added to 0.58 g (0.012 mole) of 50% sodium hydride in 15 ml of dry tetrahydrofuran. After stirring for 30 minutes at room temperature, 1.48 g (0.012 mole) of allyl bromide was added. Then the mixture was reacted for 2 hours under the same conditions. The tetrahydrofuran was distilled off under reduced pressure, and cold water was added. The resulting oil layer was extracted with benzene. The benzene layer was separated, dried over anhydrous magnesium sulfate, and concentrated to afford a white solid. Recrystallization from methanol afforded compound No. 27 in Table 2 in a yield of 35%.

Compounds Nos. 16 to 26 and 28 to 63 could be produced in the same way as in Example 4.

EXAMPLE 5

N-Methyl-N-(α-methylbenzyl)benzenesulfonamide

Benzenesulfonyl chloride (2.1 g; 0.012 mole) was added dropwise at below 40° C. to a two-layered mixture consisting of 1.35 g (0.01 mole) of N-methyl-α-phenethylamine [prepared by the method disclosed in Novzlli, J. Ame. Chem. Soc. 61, 520 (1939)] and 12 ml of a 10% aqueous solution of sodium hydroxide. On continuing the reaction for 2 hours, an oily substance formed in the lower layer. It was extracted with benzene, and dried over anhydrous magnesium sulfate. The benzene was distilled off under reduced pressure to give a colorless oily substance. Purification by silica gel column chromatography afforded pure N-methyl-N-(α-methylbenzyl)benzenesulfonamide in a yield of 98%. This compound is designated as compound No. 82 in Table 2, and its refractive index and elemental analysis values are also shown in Table 2.

Compounds Nos. 64 to 72, 74 to 77, 79 to 81, 83 to 88, and 95 to 102 shown in Table 2 could be produced in the same way as in Example 5.

EXAMPLE 6

N-Allyl-N-(2,4-dichlorobenzoyl)-4-toluenesulfonamide 4.6 g (0.02 mole) of N-allyl-2,4-dichlorobenzamide was added to 1.2 g (0.024 mole) of 50% sodium hydride in 20 ml of dry tetrahydrofuran. The mixture was stirred at room temperature for 30 minutes to react them. Then, 4.2 g (0.024 mole) of p-toluenesulfonyl chloride was added, and reacted at room temperature for 1 hour. The tetrahydrofuran was distilled off under reduced pressure. After adding cold water to the residual oil, it was extracted with benzene, dried over anhydrous magnesium sulfate, and concentrated to afford an oily substance. It was purified by silica gel chromatography to afford compound No. 42 shown in Table 2 in a yield of 68%. Its refractive index and elemental analysis values are also shown in Table 2.

Compounds Nos. 16 to 41 and 43 to 63 in Table 2 could be prepared in the same way as in Example 6.

TABLE 2

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 16 | (structure with CH₃, SO₂N—CO, Cl) | $n_D^{21}$ 1.5878 | 54.48 54.34 | 3.90 3.77 | 4.52 4.50 | 10.35 10.53 | X = Cl 11.45 11.37 |
| 17 | (structure CH₃O—, CH₃, SO₂N—CO, Cl) | 82–83.5° C. | 53.02 53.19 | 4.15 4.28 | 4.12 4.15 | 9.44 9.30 | X = Cl 10.43 10.38 |
| 18 | (structure with CH₃, SO₂N—CO, Cl, Cl) | $n_D^{25}$ 1.5912 | 48.85 48.96 | 3.22 3.41 | 4.07 4.05 | 9.32 9.44 | X = Cl 20.60 20.57 |

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 19 | Phenyl-SO$_2$N(CH$_3$)-CO-(2-Br-phenyl) | 53–54° C. | 47.47 / 47.40 | 3.41 / 3.35 | 3.95 / 3.98 | 9.05 / 9.19 | X = Br 22.56 / 22.51 |
| 20 | Phenyl-SO$_2$N(CH$_3$)-CO-(2-CH$_3$-phenyl) | 48–50° C. | 62.26 / 62.35 | 5.23 / 5.36 | 4.84 / 4.80 | 11.08 / 11.19 | — |
| 21 | Phenyl-SO$_2$N(CH$_3$)-CO-(2-OCH$_3$-3,6-diCl-phenyl) | $n_D^{25}$ 1.5791 | 48.14 / 48.03 | 3.50 / 3.38 | 3.74 / 3.75 | 8.57 / 8.66 | X = Cl 18.95 / 18.90 |
| 22 | Phenyl-SO$_2$N(C$_2$H$_5$)-CO-(2-Cl-phenyl) | $n_D^{24}$ 1.5750 | 55.64 / 55.51 | 4.36 / 4.40 | 4.33 / 4.35 | 9.90 / 9.78 | X = Cl 10.95 / 10.87 |
| 23 | (3-CH$_3$-phenyl)-SO$_2$N(C$_2$H$_5$)-CO-(2,4-diCl-phenyl) | $n_D^{25}$ 1.5768 | 51.62 / 51.53 | 4.06 / 4.18 | 3.76 / 3.74 | 8.61 / 8.53 | X = Cl 19.05 / 18.95 |
| 24 | Phenyl-SO$_2$N(n-C$_3$H$_7$)-CO-(2-Cl-phenyl) | $n_D^{24}$ 1.5650 | 56.88 / 56.92 | 4.77 / 4.73 | 4.15 / 4.08 | 9.49 / 9.31 | X = Cl 10.50 / 10.47 |
| 25 | Phenyl-SO$_2$N(i-C$_3$H$_7$)-CO-(2-Cl-phenyl) | 99–100° C. | 56.88 / 56.75 | 4.77 / 4.70 | 4.15 / 4.18 | 9.49 / 9.53 | X = Cl 10.50 / 10.43 |
| 26 | (4-F-phenyl)-SO$_2$N(i-C$_3$H$_7$)-CO-(2,4-diCl-phenyl) | $n_D^{25}$ 1.5598 | 49.24 / 49.38 | 3.62 / 3.76 | 3.59 / 3.52 | 8.22 / 8.30 | |
| 27 | Phenyl-SO$_2$N(CH$_2$CH=CH$_2$)-CO-(2-Cl-phenyl) | 65.5–66.0° C. | 57.22 / 56.98 | 4.20 / 4.31 | 4.17 / 4.13 | 9.55 / 9.32 | X = Cl 10.56 / 10.47 |
| 28 | Phenyl-SO$_2$N(CH$_2$CH=CH$_2$)-CO-(2,4-diCl-phenyl) | 78.5–79.0° C. | 51.90 / 51.83 | 3.54 / 3.46 | 3.78 / 3.91 | 8.66 / 8.70 | X = Cl 19.15 / 19.03 |
| | | | | | | | X = F |

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 29 | Phenyl-SO$_2$N(CH$_2$CH=CH$_2$)-CO-O-(2-F-C$_6$H$_4$) | 39.0–40.0° C. | 60.17 / 59.98 | 4.42 / 4.37 | 4.39 / 4.43 | 10.04 / 9.90 | 5.95 / 5.90 |
| 30 | Phenyl-SO$_2$N(CH$_2$CH=CH$_2$)-CO-O-(2-I-C$_6$H$_4$) | 51.5–52.5° C. | 44.97 / 45.31 | 3.30 / 3.17 | 3.28 / 3.35 | 7.50 / 7.63 | 29.71 / 29.65  (X = I) |
| 31 | Phenyl-SO$_2$N(CH$_2$CH=CH$_2$)-CO-O-(2-Cl-C$_6$H$_4$) | 49.0–49.5° C. | 57.22 / 56.96 | 4.20 / 4.27 | 4.17 / 4.21 | 9.55 / 9.42 | 10.56 / 10.39  (X = Cl) |
| 32 | Phenyl-SO$_2$N(CH$_2$CH=CH$_2$)-CO-O-(2,6-Cl$_2$-C$_6$H$_3$) | 111.0–112.0° C. | 51.90 / 52.04 | 3.54 / 3.65 | 3.78 / 3.83 | 8.66 / 8.54 | 19.15 / 19.03  (X = Cl) |
| 33 | Phenyl-SO$_2$N(CH$_2$CH=CH$_2$)-CO-O-(2,3,6-Cl$_3$-C$_6$H$_2$) | 96.0–98.0° C. | 47.48 / 47.57 | 2.99 / 3.08 | 3.46 / 3.52 | 7.92 / 7.74 | 26.28 / 26.15  (X = Cl) |
| 34 | Phenyl-SO$_2$N(CH$_2$CH=CH$_2$)-CO-O-(2-CH$_3$-C$_6$H$_4$) | 54.5–55.0° C. | 64.74 / 65.20 | 5.43 / 5.31 | 4.44 / 4.52 | 10.17 / 10.29 | — |
| 35 | Phenyl-SO$_2$N(CH$_2$CH=CH$_2$)-CO-O-(3-CH$_3$-C$_6$H$_4$) | 57.0–57.5° C. | 64.74 / 64.80 | 5.43 / 5.33 | 4.44 / 4.49 | 10.17 / 10.26 | — |
| 36 | Phenyl-SO$_2$N(CH$_2$CH=CH$_2$)-CO-O-(2-OCH$_3$-C$_6$H$_4$) | 86.0–87.0° C. | 61.61 / 61.45 | 5.17 / 5.24 | 4.23 / 4.35 | 9.68 / 9.52 | — |
| 37 | Phenyl-SO$_2$N(CH$_2$CH=CH$_2$)-CO-O-(4-OCH$_3$-C$_6$H$_4$) | 56.0–56.5° C. | 61.61 / 61.50 | 5.17 / 5.23 | 4.23 / 4.15 | 9.68 / 9.75 | — |
| 38 | Phenyl-SO$_2$N(CH$_2$CH=CH$_2$)-CO-O-(2,6-Cl$_2$-3-OCH$_3$-C$_6$H$_2$) | n$_D^{26}$1.5775 | 51.01 / 50.90 | 3.78 / 3.85 | 3.50 / 3.42 | 8.01 / 8.06 | 17.72 / 17.65  (X = Cl) |

X = Cl

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 39 | CH₃–C₆H₄–SO₂N(CH₂CH=CH₂)–CO–C₆H₄–Cl (2-methyl, 2'-Cl) | $n_D^{26}$ 1.5700 | 58.36 / 58.02 | 4.61 / 4.81 | 4.00 / 3.97 | 9.17 / 9.09 | 10.14 / 10.10 |
| 40 | CH₃–C₆H₄–SO₂N(CH₂CH=CH₂)–CO–C₆H₄–Cl (3-methyl, 2'-Cl) | $n_D^{26}$ 1.5735 | 58.36 / 58.24 | 4.61 / 4.75 | 4.00 / 3.95 | 9.17 / 9.10 | X = Cl 10.14 / 10.07 |
| 41 | CH₃–C₆H₄–SO₂N(CH₂CH=CH₂)–CO–C₆H₃–Cl₂ (3-methyl, 2',4'-Cl₂) | $n_D^{26}$ 1.5805 | 53.13 / 53.01 | 3.93 / 3.85 | 3.65 / 3.58 | 8.34 / 8.55 | X = Cl 18.45 / 18.53 |
| 42 | CH₃–C₆H₄–SO₂N(CH₂CH=CH₂)–CO–C₆H₃–Cl₂ (4-methyl, 2',4'-Cl₂) | $n_D^{25}$ 1.5649 | 53.13 / 53.20 | 3.93 / 3.85 | 3.65 / 3.50 | 8.34 / 8.46 | X = Cl 18.45 / 18.50 |
| 43 | C₂H₅–C₆H₄–SO₂N(CH₂CH=CH₂)–CO–C₆H₃–Cl₂ | $n_D^{28}$ 1.5796 | 54.28 / 54.34 | 4.30 / 4.41 | 3.52 / 3.45 | 8.05 / 8.12 | X = Cl 17.80 / 17.72 |
| 44 | Cl–C₆H₄–SO₂N(CH₂CH=CH₂)–CO–C₆H₃–Cl₂ | $n_D^{26}$ 1.5953 | 47.48 / 47.45 | 2.99 / 3.05 | 3.46 / 3.58 | 7.92 / 7.80 | X = Cl 26.28 / 26.35 |
| 45 | Cl–C₆H₄–SO₂N(CH₂CH=CH₂)–CO–C₆H₄–Cl (3-Cl, 2'-Cl) | 81.0–82.0° C. | 51.90 / 51.75 | 3.54 / 3.65 | 3.78 / 3.71 | 8.66 / 8.68 | X = Cl 19.15 / 19.30 |
| 46 | Cl–C₆H₄–SO₂N(CH₂CH=CH₂)–CO–C₆H₃–Cl₂ (3-Cl, 2',4'-Cl₂) | 69.5–70.0° C. | 47.48 / 47.62 | 2.99 / 3.03 | 3.46 / 3.30 | 7.92 / 7.85 | X = Cl 26.28 / 26.36 |
| 47 | F–C₆H₄–SO₂N(CH₂CH=CH₂)–CO–C₆H₄–Cl | $n_D^{18}$ 1.5712 | 54.31 / 54.34 | 3.70 / 3.63 | 3.96 / 4.05 | 9.06 / 9.22 | X = Cl 10.02 / 9.91 |
| 48 | Br–C₆H₄–SO₂N(CH₂CH=CH₂)–CO–C₆H₄–Cl | 57.0–59.5° C. | 46.34 / 46.52 | 3.16 / 3.24 | 3.38 / 3.26 | 7.73 / 7.64 | — / — |
| 49 | CH₃O–C₆H₄–SO₂N(CH₂CH=CH₂)–CO–C₆H₄–Cl | 43.0–45.0° C. | 55.81 / 55.68 | 4.41 / 4.60 | 3.83 / 3.75 | 8.77 / 8.90 | X = Cl 9.69 / 9.65 |

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 50 | Ph-SO$_2$N(CH$_2$CH=CH$_2$)-CO-O-(2,3,6-trichloro-4-methoxyphenyl) | 81.0–82.0° C. | 44.20<br>44.14 | 3.55<br>3.29 | 3.22<br>3.28 | 7.38<br>7.53 | X = Cl<br>24.47<br>24.61 |
| 51 | Ph-SO$_2$N(n-C$_4$H$_9$)-CO-O-(2-chlorophenyl) | n$_D^{24}$1.5575 | 58.03<br>58.18 | 5.16<br>5.34 | 3.98<br>3.95 | 9.11<br>9.04 | X = Cl<br>10.08<br>10.13 |
| 52 | Ph-SO$_2$N(iso-C$_4$H$_9$)-CO-O-(2-chlorophenyl) | n$_D^{24}$1.5550 | 58.03<br>58.18 | 5.16<br>5.25 | 3.98<br>3.98 | 9.11<br>9.15 | X = Cl<br>10.08<br>10.01 |
| 53 | Ph-SO$_2$N(sec-C$_4$H$_9$)-CO-O-(2-chlorophenyl) | 50.0–52.0° C. | 58.03<br>57.94 | 5.16<br>5.07 | 3.98<br>3.84 | 9.11<br>9.21 | X = Cl<br>10.08<br>10.12 |
| 54 | Ph-SO$_2$N(n-C$_5$H$_{11}$)-CO-O-(2-chlorophenyl) | n$_D^{24}$1.5580 | 59.09<br>58.94 | 5.51<br>5.39 | 3.83<br>3.85 | 8.76<br>8.90 | X = Cl<br>9,69<br>9.48 |
| 55 | Ph-SO$_2$N(n-C$_7$H$_{15}$)-CO-O-(2-chlorophenyl) | 62.5–63.5° C. | 60.98<br>61.01 | 6.14<br>6.16 | 3.56<br>3.51 | 8.14<br>8.18 | X = Cl<br>9.00<br>8.79 |
| 56 | Ph-SO$_2$N(n-C$_8$H$_{17}$)-CO-O-(2-chlorophenyl) | 62.0–63.5° C. | 61.82<br>61.78 | 6.42<br>6.50 | 3.43<br>3.40 | 7.86<br>7.91 | X = Cl<br>8.69<br>8.67 |
| 57 | Ph-SO$_2$N(n-C$_9$H$_{19}$)-CO-O-(2-chlorophenyl) | 88.0–89.0° C. | 62.62<br>62.53 | 6.69<br>6.64 | 3.32<br>3.35 | 7.60<br>7.66 | X = Cl<br>8.40<br>8.37 |
| 58 | Ph-SO$_2$N(n-C$_{10}$H$_{21}$)-CO-O-(2-chlorophenyl) | 42.0–43.5° C. | 63.36<br>63.45 | 6.94<br>6.89 | 3.21<br>3.30 | 7.35<br>7.38 | X = Cl<br>8.13<br>8.15 |
| 59 | Ph-SO$_2$N(n-C$_{12}$H$_{25}$)-CO-O-(2-chlorophenyl) | n$_D^{26}$1.5327 | 63.76<br>63.52 | 7.58<br>7.53 | 3.10<br>3.20 | 7.09<br>7.11 | X = Cl<br>7.84<br>7.80 |

X = Cl

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 60 | PhSO₂N(CH₂CH₂CH₂N(CH₃)₂)—CO—C₆H₄Cl(o) | $n_D^{24}$ 1.5584 | 56.76 | 5.56 | 7.36 | 8.42 | 9.31 |
| | | | 56.88 | 5.62 | 7.30 | 8.48 | 9.28 |
| 61 | PhSO₂N(CH₂CN)—CO—C₆H₄Cl(o) | $n_D^{24}$ 1.5760 | 53.81 | 3.31 | 8.37 | 9.58 | X = Cl 10.57 |
| | | | 53.73 | 3.22 | 8.40 | 9.53 | 10.70 |
| 62 | PhSO₂N(CH₂CH₂CH₂OCH₃)—CO—C₆H₄Cl(o) | $n_D^{21}$ 1.5650 | 55.50 | 4.93 | 3.81 | 8.72 | X = Cl 9.64 |
| | | | 55.37 | 4.82 | 3.84 | 8.58 | 9.81 |
| 63 | PhSO₂N(CH₂C≡CH)—CO—C₆H₄Cl(o) | $n_D^{25}$ 1.5778 | 57.57 | 3.62 | 4.20 | 9.61 | X = Cl 10.62 |
| | | | 57.63 | 3.75 | 4.18 | 9.78 | 10.55 |
| 64 | PhSO₂N(CH₃)—C(CH₃)₂—Ph | 93.0° C. | 66.40 | 6.62 | 4.84 | 11.08 | — |
| | | | 66.25 | 6.58 | 4.75 | 11.00 | — |
| 65 | PhSO₂N(C₂H₅)—C(CH₃)₂—Ph | 65.0–66.0° C. | 67.29 | 6.98 | 4.62 | 10.57 | — |
| | | | 67.35 | 7.02 | 4.58 | 10.52 | — |
| 66 | PhSO₂N(n-C₃H₇)—C(CH₃)₂—Ph | 79.0–80.0° C. | 68.10 | 7.30 | 4.41 | 10.10 | — |
| | | | 68.05 | 7.21 | 4.39 | 10.15 | — |
| 67 | PhSO₂N(CH₂—CH=CH₂)—C(CH₃)₂—Ph | 74.5–75.0° C. | 68.54 | 6.71 | 4.44 | 10.17 | — |
| | | | 68.38 | 6.65 | 4.49 | 10.05 | — |
| 68 | PhSO₂N(CH₂—C≡CH)—C(CH₃)₂—Ph | $n_D^{21}$ 1.5750 | 68.98 | 6.11 | 4.47 | 10.23 | — |
| | | | 68.85 | 6.08 | 4.49 | 10.20 | — |
| 69 | PhSO₂N(CH₂—C(CH₃)=CH₂)—C(CH₃)₂—Ph | 47.0–48.0° C. | 69.29 | 7.04 | 4.25 | 9.73 | — |
| | | | 69.09 | 7.08 | 4.13 | 9.82 | — |
| 70 | PhSO₂N(n-C₄H₉)—C(CH₃)₂—Ph | 68.0° C. | 68.84 | 7.60 | 4.23 | 9.67 | — |
| | | | 68.75 | 7.64 | 4.18 | 9.75 | — |
| 71 | PhSO₂N(n-C₆H₁₃)—C(CH₃)₂—Ph | $n_D^{21}$ 1.5450 | 70.23 | 8.14 | 3.90 | 8.92 | — |
| | | | 70.05 | 8.17 | 3.85 | 8.99 | — |

TABLE 2-continued

| Compound No. | Structural formula | Melting point or refractive index | C (calc/found) | H | N | S | X |
|---|---|---|---|---|---|---|---|
| 72 | Phenyl-SO$_2$N(n-C$_{12}$H$_{25}$)-C(CH$_3$)(CH$_3$)-phenyl | $n_D^{21}$ 1.5190 | 73.09 / 73.15 | 9.32 / 9.35 | 3.16 / 3.10 | 7.23 / 7.18 | — |
| 73 | Phenyl-SO$_2$N(CH$_2$OCH$_3$)-C(CH$_3$)(CH$_3$)-phenyl | $n_D^{21}$ 1.5530 | 63.92 / 63.86 | 6.63 / 6.48 | 4.39 / 4.50 | 10.04 / 10.12 | — |
| 74 | (2-CH$_3$-phenyl)-SO$_2$N(CH$_2$—CH=CH$_2$)-C(CH$_3$)(CH$_3$)-phenyl | 63.0–66.0° C. | 69.27 / 69.20 | 7.04 / 7.08 | 4.25 / 4.21 | 9.73 / 9.78 | — |
| 75 | (4-CH$_3$-phenyl)-SO$_2$N(CH$_2$—CH=CH$_2$)-C(CH$_3$)(CH$_3$)-phenyl | $n_D^{27}$ 1.5676 | 69.27 / 69.13 | 7.04 / 7.08 | 4.25 / 4.21 | 9.73 / 9.76 | — |
| 76 | (4-CH$_3$O-phenyl)-SO$_2$N(CH$_2$—CH=CH$_2$)-C(CH$_3$)(CH$_3$)-phenyl | $n_D^{27}$ 1.5710 | 66.06 / 66.15 | 6.71 / 6.67 | 4.06 / 4.10 | 9.28 / 9.22 | — |
| 77 | (4-Cl-phenyl)-SO$_2$N(CH$_2$—CH=CH$_2$)-C(CH$_3$)(CH$_3$)-phenyl | $n_D^{27}$ 1.5770 | 61.79 / 61.71 | 5.76 / 5.79 | 4.00 / 4.06 | 9.17 / 9.12 | X = Cl 10.13 / 10.09 |
| 78 | Phenyl-SO$_2$N(CH$_2$—CH=CH$_2$)-C(CH$_3$)(CH$_3$)-(4-Cl-phenyl) | $n_D^{26}$ 1.5672 | 61.79 / 61.68 | 5.76 / 5.71 | 4.00 / 3.95 | 9.17 / 9.23 | X = Cl 10.13 / 10.10 |
| 79 | Phenyl-SO$_2$N(CH$_2$CH=CH$_2$)-C(CH$_3$)(CH$_3$)-(CH$_3$-phenyl) (mixture of o-, m-, p-isomers) | 61.0–63.0° C. | 69.26 / 69.17 | 7.04 / 7.10 | 4.25 / 4.20 | 9.73 / 9.78 | — |
| 80 | (2,5-diCH$_3$-phenyl)-SO$_2$N(CH$_2$—CH=CH$_2$)-C(CH$_3$)(CH$_3$)-phenyl | $n_D^{26}$ 1.5653 | 69.93 / 69.95 | 7.34 / 7.32 | 4.08 / 4.10 | 9.34 / 9.30 | — |
| 81 | (4-C$_2$H$_5$-phenyl)-SO$_2$N(CH$_2$—CH=CH$_2$)-C(CH$_3$)(CH$_3$)-phenyl | $n_D^{26}$ 1.5630 | 69.93 / 69.92 | 7.34 / 7.40 | 4.08 / 4.13 | 9.34 / 9.29 | — |
| 82 | Phenyl-SO$_2$N(CH$_3$)-CH(CH$_3$)-phenyl | 78.0–79.0° C. | 65.42 / 65.34 | 6.22 / 6.19 | 5.09 / 5.15 | 11.65 / 11.71 | — |
| 83 | Phenyl-SO$_2$N(C$_2$H$_5$)-CH(CH$_3$)-phenyl | 62.0–62.5° C. | 66.40 / 64.48 | 6.62 / 6.56 | 4.84 / 4.79 | 11.08 / 11.16 | — |
| 84 | Phenyl-SO$_2$N(n-C$_3$H$_7$)-CH(CH$_3$)-phenyl | 50.0–52.0° C. | 67.29 / 67.21 | 6.98 / 6.92 | 4.62 / 4.70 | 10.57 / 10.65 | — |

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 85 | Ph-SO$_2$N(CH$_2$-CH=CH$_2$)-CH(CH$_3$)-Ph | $n_D^{27}$1.5598 | 67.74<br>67.80 | 6.35<br>6.30 | 4.65<br>4.72 | 10.64<br>10.49 | —<br>— |
| 86 | Ph-SO$_2$N(n-C$_4$H$_9$)-CH(CH$_3$)-Ph | $n_D^{27}$1.5507 | 68.10<br>68.25 | 7.30<br>7.25 | 4.41<br>4.37 | 10.10<br>10.26 | —<br>— |
| 87 | Ph-SO$_2$N(n-C$_6$H$_{13}$)-CH(CH$_3$)-Ph | 47.0–48.5° C. | 69.52<br>69.39 | 7.88<br>7.95 | 4.04<br>4.01 | 9.28<br>9.37 | —<br>— |
| 88 | Ph-SO$_2$N(n-C$_{12}$H$_{25}$)-CH(CH$_3$)-Ph | $n_D^{27}$1.5066 | 72.68<br>72.52 | 9.15<br>9.18 | 3.26<br>3.20 | 7.46<br>7.52 | —<br>— |
| 89 | Ph-SO$_2$N(CH$_2$-CH=CH$_2$)-CH(CH$_3$)-(2-Cl-C$_6$H$_4$) | 65.0–67.5° C. | 60.79<br>60.65 | 5.40<br>5.35 | 4.17<br>4.23 | 9.55<br>9.61 | X = Cl<br>10.56<br>10.63 |
| 90 | Ph-SO$_2$N(CH$_2$-CH=CH$_2$)-CH(CH$_3$)-(3-Cl-C$_6$H$_4$) | $n_D^{26}$1.5705 | 60.79<br>60.68 | 5.40<br>5.47 | 4.17<br>4.09 | 9.55<br>9.63 | X = Cl<br>10.56<br>10.65 |
| 91 | Ph-SO$_2$N(CH$_2$-CH=CH$_2$)-CH(CH$_3$)-(4-Cl-C$_6$H$_4$) | $n_D^{26}$1.5720 | 60.79<br>60.65 | 5.40<br>5.29 | 4.17<br>4.09 | 9.55<br>9.39 | X = Cl<br>10.56<br>10.70 |
| 92 | Ph-SO$_2$N(CH$_2$-CH=CH$_2$)-CH(CH$_3$)-(2,4-Cl$_2$-C$_6$H$_3$) | $n_D^{26}$1.5821 | 55.14<br>55.05 | 4.63<br>4.69 | 3.78<br>3.75 | 8.66<br>8.71 | X = Cl<br>19.15<br>19.03 |
| 93 | Ph-SO$_2$N(CH$_2$-CH=CH$_2$)-CH(CH$_3$)-(4-CH$_3$-C$_6$H$_4$) | $n_D^{27}$1.5598 | 68.54<br>68.45 | 6.71<br>6.76 | 4.44<br>4.39 | 10.17<br>10.28 | —<br>— |
| 94 | Ph-SO$_2$N(CH$_2$-CH=CH$_2$)-CH(CH$_3$)-(4-OCH$_3$-C$_6$H$_4$) | $n_D^{26}$1.5670 | 65.23<br>65.12 | 6.39<br>6.35 | 4.23<br>4.31 | 9.68<br>9.79 | —<br>— |
| 95 | (2,4-(CH$_3$)$_2$-C$_6$H$_3$)-SO$_2$N(CH$_2$-CH=CH$_2$)-CH(CH$_3$)-Ph | $n_D^{26}$1.5666 | 69.27<br>69.25 | 7.04<br>7.01 | 4.25<br>4.28 | 9.73<br>9.69 | —<br>— |
| 96 | (2,5-(CH$_3$)$_2$-C$_6$H$_3$)-SO$_2$N(CH$_2$-CH=CH$_2$)-CH(CH$_3$)-Ph | $n_D^{26}$1.5671 | 69.27<br>69.30 | 7.04<br>7.02 | 4.25<br>4.15 | 9.73<br>9.75 | —<br>— |

TABLE 2-continued

| Compound No. | Structural formula | Melting point or refractive index | Elemental analysis values (%) (the upper row: calculated the lower row: found) | | | | |
|---|---|---|---|---|---|---|---|
| | | | C | H | N | S | X |
| 97 | CH₃—⟨phenyl⟩—SO₂N(CH₂CH=CH₂)—CH(CH₃)—⟨phenyl⟩ | $n_D^{27}$ 1.5647 | 68.54<br>68.39 | 6.71<br>6.65 | 4.44<br>4.50 | 10.17<br>10.30 | —<br>— |
| 98 | C₂H₅—⟨phenyl⟩—SO₂N(CH₂CH=CH₂)—CH(CH₃)—⟨phenyl⟩ | $n_D^{26}$ 1.5630 | 69.26<br>69.35 | 7.04<br>7.11 | 4.25<br>4.20 | 9.73<br>9.65 | —<br>— |
| 99 | CH₃O—⟨phenyl⟩—SO₂N(CH₂CH=CH₂)—CH(CH₃)—⟨phenyl⟩ | $n_D^{27}$ 1.5700 | 65.23<br>65.15 | 6.39<br>6.46 | 4.23<br>4.19 | 9.68<br>9.76 | —<br>— |
| 100 | Cl—⟨phenyl⟩—SO₂N(CH₂CH=CH₂)—CH(CH₃)—⟨phenyl⟩ | $n_D^{27}$ 1.5748 | 60.79<br>60.65 | 5.40<br>5.32 | 4.17<br>4.25 | 9.55<br>9.63 | X=Cl<br>10.56<br>10.65 |
| 101 | ⟨phenyl⟩—SO₂N(CH₂C≡CH)—CH(CH₃)—⟨phenyl⟩ | $n_D^{27}$ 1.5891 | 68.20<br>68.12 | 5.72<br>5.75 | 4.68<br>4.61 | 10.71<br>10.82 | —<br>— |
| 102 | ⟨phenyl⟩—SO₂N(CH₂—C(CH₃)=CH₂)—CH(CH₃)—⟨phenyl⟩ | $n_D^{27}$ 1.5621 | 68.54<br>68.39 | 6.71<br>6.75 | 4.44<br>4.40 | 10.17<br>10.29 | —<br>— |

The compounds of formula (I) provided by this invention have superior herbicidal activities, and are useful as active ingredients of herbicides for controlling various weeds in agricultural crops. Examples of weeds which can be controlled by the compounds of formula (I) of this invention are various species of barnyard grass (such as *Echinochloa crus-galli* Beauv., *Echinochloa crus-galli* var. oryzicola Ohwi, and *Echinochloa crus-galli* Subsp. genuina var. echinata Honda), spikerush (*Eleocharis pellucida* Presl), sedge sp. (*Cyperus hakonensis* saiat), umbrella plant (*Cyperus difformis* L.), pipewort (*Eriocaulon sieboldtianum* Sieb), waterwort (*Elatine triandra*), redstem sp. (*Rotala indica* Koehne), bulrush (*Scirpus juncoides* Roxb), redstem sp. (*Ammannia multiflorn* Roxb.), false pimpernel (*Lindernia pyxidaria* L.), and slender spikerush (*Eleocharis acicularis* Roem. et Schalt var. longiseta Svenson). These examples are not limitative, and it should be understood that the compounds of formula (I) of this invention exhibit herbicidal effects also against other kinds of weeds.

It has been found that the compounds of formula (I) of this invention exhibit marked effects in controlling weeds which occur in fields containing much water, such as a paddy field, rather than those which occur in dry upland fields.

Thus, the compounds of formula (I) exhibit excellent control effects against various species of barnyard grass, especially *Echinochloa crus-gallie* Beauv. which is a very hazardous weed in an aquatic paddy and is considered as one of the five greatest weeds in the world. This weed grows in paddy fields, especially submerged paddy fields, throughout the world. The compounds of formula (I) have the ability to inhibit the germination of the barnyard grass strongly and to prevent its growth in paddy fields.

Moreover, the compounds of formula (I) are very characteristic in that they have excellent selective herbicidal activity which ensures substantial freedom from phytotoxicity to useful agricultural crops such as rice.

Many herbicides have heretofore been suggested for application to paddy fields, and some have come into actual use. Almost none of them, however, have selectivity in physiological herbicidal action between barnyard grass and rice plant. The conventional methods for weed killing in paddy fields are directed to the treatment of paddy fields in the rice growing stage (including the transplanting stage) to control the sprouting of barnyard grass. They are based either on the utilization of the differences in resistance to herbicides between barnyard grass and rice plant according to the differences in their growing stages, or on the principle of chemical adsorption in the upper layer of soil ("artifical selectivity") whereby rice plants are transplated in such a manner that their roots are located below the herbicide-treated layer, and barnyard grass in the upper layer is controlled while protecting the rice plants from the herbicide.

Barnyard grss is a graminaceous weed, as is rice, and they physiologically resemble each other very well. Hence, controlling of barnyard grass with herbicidal chemicals often casuses phytotoxicity to rice plant, and it is extremely difficult to control this weed selectively in paddy fields. Barnyard grass has therefore been considered to be difficult to eradicate in paddy fields, and there has been a strong demand for the advent of herbicides which can selectively control barnyard grass.

The compounds of formula (I) of this invention meet this demand of agriculture. They have the excellent property of acting selectively on the seeds and seedlings of barnyard grass to strongly inhibit their germination, but causing no substantial phytotoxicity to rice plant. This property renders the compounds of formula (I) very suitable as active ingredients of herbicides for application to paddy fields.

The superior herbicidal activity of the compounds (I) of this invention can be demonstrated by the experimental fact that when N-allyl-N-(2-chlorobenzoyl)benzenesulfonamide was applied at a rate of 62.5 g per 10 ares to a paddy field where rice plant and barnyard grass were simultaneously sown, the germination of the barnyard grass was completely inhibited, whereas the rice plant showed normal emergence and growth without any phytotoxicity, and that even when the rate of the compound applied was increased to 1,000 g per 10 ares, the rice plant showed normal germination and growth without any phytotoxicity. Thus, the compound of this invention, when applied in an amount about 20 times as large as the amount required for completely controlling barnyard grass, does not exert any substantial effect on the germination and growth of rice plant.

Such a high selectivity of the compounds of this invention between barnyard grass and rice plant is ascribable presumably to the specific physiological activities of the compounds of this invention against barnyard grass and rice plant. This superior selectivity cannot be expected from the conventional herbicides available for application to paddy fields.

The compound of formula (I) of this invention may be applied directly as a herbicide. Generally, however, it is formulated into a herbicidal composition by mixing it with inert liquid or solid carriers or diluents which are commonly employed in herbicide formulations.

In the present invention, any inert liquid or solid carriers or diluents known in the art can be used. Examples of the inert solid carrier or diluent are kaolin, diatomaceous earth, talc, bentonite, silica, and clay minerals. Examples of the inert liquid carrier or diluent are water, xylene, toluene, benzene, N,N-dimethyl formamide, dimethyl sulfoxide, and liquefied gases such as tetrafluoroethane.

In addition to the inert liquid or solid carrier or diluent, the herbicidal composition may, as needed, contain surface-active agents such as polyoxyethylene monolaurate or polyethylene sorbitol in usual amounts chosen according to the form of the herbicidal composition.

The herbicidal composition may contain the active compound of formula (I) in an amount of at least 0.5% by weight, preferably 1 to 99% by weight, more preferably 2 to 80% by weight, based on the weight of the composition itself.

The herbicidal composition can be in any conventional forms such as a dust, granule, wettable powder, solution, emulsifiable concentrate, or spray according to the method of application. Any methods of formulation known in the art can be used for this purpose. For example, when making a dust, granule or wettable powder, at least one active compound of formula (I) is mixed with at least one inert solid carrier or diluent. The mixture is pulverized and mixed uniformly with a suitable amount of a surface active agent. The solution or emulsifiable concentrate can be prepared by dissolving or dispersing at least one active compound of formula (I) in at least one inert liquid carrier or diluent, followed, if desired, by adding a surface active agent.

Conveniently, the amount of the active compound of formula (I) is 3 to 20% by weight for the dust and granule, 25 to 75% by weight for the wettable powder, and 20 to 50% by weight for the solution and emulsifiable concentrate, all based on the weight of the resulting composition.

The herbicidal composition may further contain agricultural chemicals commonly used in cultivating agricultural crops, such as fungicides, insecticides, nematocides, and fertilizers. Typical examples of the fungicides are Benomyl [methyl 1-(n-butylaminocarbonyl)-1H-benzimidazol-2-yl-carbamate], Hymexazol (5-methyl-3-isoxazolol), Captan [3a,4,7,7a-tetrahydro-N-(trichloromethanesulphenyl) phthalimide], and Zineb [zinc ethylenebis(dithiocarbamate]. Examples of the insecticides are Disulfoton (O,O-diethyl S-2-ethylthioethyl phosphorodithioate) and Propoxur (2-isopropoxyphenyl methylcarbamate). Examples of the nematocides are Methomyl [S-methyl N-(methylcarbamoyloxy) thioacetamidate] and Alidicarb [2-methyl-2-(methylthio) propionaldehyde O-methylcarbamoyloxime].

It is also possible to incorporate at least one other herbicidally active compound used heretofore in the art into the herbicidal composition of this invention. This frequently brings about a high herbicidal effect against a broad spectrum of weeds. Examples of the other herbicidally active compounds include MCP (2-methyl-4-chlorophenoxy acetic acid), TOK (2,4-dichlorophenyl-4'-nitrophenyl ether), Benthiocarb[S-4-chlorobenzyl-N,N-diethylthiocarbamate], Molinate (S-ethyl-N,N-hexamethylene thiolcarbamate), Oxadiazon[2-tert-butyl-4-(2,4-dichloro-5-isopropoxyphenyl-5-oxo-1,3,4-oxadiazoline], and Butachlor [2-chloro-2',6'-diethyl-N-(butoxymethyl)acetanilide]. It should be understood that these examples are not limitative, and other active compounds can be equally incorporated in the herbicidal composition of this invention as needed.

The herbicidal compositions of this invention containing these other herbicidally active compounds are especially useful for applicaion to paddy fields in the rice growing stage, for example to a paddy field in which transplantation has ended.

The herbicide containing the compound of formula (I) as an active ingredient can be used to control various weeds in areas where agricultural crops are cultivated. In particular, the herbicide of this invention is effective against weeds in wet paddies rather than dry fields, and exhibits a very strong selective herbicidal effect against barnyard grass which accompanies rice plant in paddy fields, such as *Echinochloa crus-galli* Beauv.

Herbicides containing as active ingredients 2,4,6-trichlorophenyl-4'-nitrophenyl ether (MO or CNP), S-(4-chlorobenzyl)-N,N-diethylthiocarbamate (Benthiocarb), 2-chloro-2',6'-diethyl-N-(butoxymethyl)acetanilide (Butachlor), and S-ethyl-N,N-hexamethylenethiolcarbamate (Molinate), which now gain widespread acceptance for application to paddy fields, do not show selectivity between barnyard grass and rice plant in the germinating stage, nor are they absolutely safe to transplanted rice plants in the early stage of growth. With these conventional herbicides, the risk of phytotoxicity cannot be avoided in the event of changes in the environmental condition of paddy fields, for example when rice plants are transplanted shallow at the soil surface, the soil is sandy, the water leaks, root growth is abnormal, or the temperature becomes unusually high.

Since the herbicide provided by this invention is based on physiological selectivity, it has the advantage of being applicable to all growing stages of rice plants ranging from the germinating to the growing stage, and being substantially free from phytotoxicity to rice plants by changes in environmental conditions. Thus, it contributes greatly to the cultivation of agricultural crops.

Heretofore, 3',4'-dichloropropionanilide (Propanil) has been used world wide as an agent having selective activity against barnyard grass in a paddy field. Propanil, however, is an agent suited for foliar application and has no effect of inhibiting germination. In contrast, the herbicide of this invention exhibits far higher selective activity during the emergence of barnyard grass and rice plant than Propanil, and it is no exaggeration to say that the herbicide of this invention is an epoch-making weed killer having no equal among known herbicides of this kind.

As a result of fundamental and applied tests on the herbicides of this invention, it has been found that most effective, and most preferred, herbicides of this invention are those containing N-allyl-N-(2-chlorobenzoyl)-benzenesulfonamide, N-allyl-N-(2,4-dichlorobenzoyl)-benzenesulfonamide, N-propargyl-N-(2-chlorobenzoyl)benzenesulfonamide, N-allyl-N-($\alpha,\alpha$-dimethylbenzyl)benzenesulfonamide, and N-allyl-N-($\alpha$-methylbenzyl)benzenesulfonamide as active ingredients. These active compounds commonly have the property of strongly inhibiting the germination of barnyard grass without affecting rice plants in emergence. There is, however, a slight difference in activity among these compounds. For example, herbicides containing benzoyltype active compounds have long persistence in soil and can inhibit the growth of weeds for long periods of time. Herbicides containing benzyl-type active compounds, on the other hand, have a very wide range of selectivity between barnyard grass and rice plant immediately after emergence.

In use, the herbicide of this invention containing the active ingredient of formula (I) is applied to the locus to be protected from weeds.

Thus, according to still another aspect of this invention, there is provided a method for controlling weeds in agricultural crops which comprises applying the compound of general formula (I) described hereinbefore to the locus to be protected from the weeds.

The time of application of the compound of formula (I) is not strictly limited, and differs according to the agricultural crops and/or the weeds to be controlled. Generally, in order for the active compound of this invention to exhibit the best herbicidal effect, it is most convenient to apply it just before the weeds to be controlled sprout, or during their germinating stage. It is of course possible to apply it to weeds after emergence, and this brings about some extent of control effect.

There is no particular restriction on the locus to which the active compound of this invention can be applied. It can be applied to various types of agricultural land as is the case with conventional herbicides. It can be best applied however to wet paddies, especially aquatic paddies in the submerged state, and when applied to upland fields of low water content, the active compound of this invention tends to have a somewhat decreased herbicidal effect.

In order for the herbicide of this invention to exhibit its herbicidal effect most, it is applied to a field in a submerged condition before or during the germination of weeds.

The active compounds of formula (I) of this invention exhibit herbicidal effects against the various weeds described hereinabove, but have excellent effects of inhibiting germination of various kinds of barnyard grass, especially *Echinochloa crus-galli* Beauv. which accompany rice plants, without any substantial toxicity to rice plant. Thus, the active compounds of formula (I) can be effectively applied to control barnyard grass selectively and protect rice plants therefrom.

The rate of application of the active compound of formula (I) is not critical, and can be varied widely according to the type of the active compound, the time of application, the procedure of application, etc. It is advantageous that the rate of application of the active compound of formula (I) is generally at least 25 g, preferably 50 to 1000 g, more preferably 100 to 500 g, per 10 ares.

The method of application may be any conventional method. For example, the herbicidal composition of this invention may be sprayed onto the locus to be protected from weeds from above the ground or from the air. Or it may be sprayed together with the seeds of an agricultural crop at the time of seeding the crop.

Furthermore, according to the present invention, seeds of a crop may be dipped prior to sowing in an aqueous liquid containing the active compound of this invention to control the germination of weed seeds that may be present in admixture with the crop seeds.

The active compounds of formula (I) of this invention have little toxicity on useful agricultural crops and low mammalian toxicity, and therefore are very suitable as herbicides.

The following Examples further illustrate the formulation of the herbicides provided by the present invention, and their selective herbicidal activities.

In these Examples, all parts and percentages are by weight. The numbers of the compounds refer to those given in Table 2.

EXAMPLE A (WETTABLE POWDER)

40 Parts of compound No. 27, 55 parts of a 2:1 mixture of Zeeklite and Kunilite (a registered trademark of a product of Kunimine Kabushiki Kaisha), and Sorpol 800 as a surfactant (a registered trademark for a product of Toho Kagaku Kogyo K.K.) were mixed and pulverized to form a 40% wettable powder.

EXAMPLE B (EMULSIFIABLE CONCENTRATE)

25 Parts of compound No. 85, 65 parts of benzene and 10 parts of Sorpol 800 as a surfactant were mixed and dissolved to form a 25% emulsifiable concentrate.

EXAMPLE C (GRANULE)

Five parts of compound No. 67, 50 parts of bentonite, 40 parts of Kunilite and 5 parts of Sorpol 800 as a surfactant were mixed, and pulverized. Then, 10 parts of water was added, and the mixture was uniformly stirred to form a paste. The paste was extruded through a hole with a diameter of 0.7 mm, dried, and then cut to a length of 1 to 2 mm to form a 5% granule.

EXAMPLE D

Pots (1/5000 are) were filled with a paddy soil in the muddy state, and barnyard grass (*Echinochloa crus-galli* Beauv.) and other broad-leaved weeds (waterwort, pipewort, umbrella plant, spikerush, sedge sp., red stem, and false pimpernel), bulurusk, and slender spikerush were sown or planted. At the same time, 10 germinated rice seeds (variety: Nihonbare) were sown, and two rice seedlings in the 3-lead stage when planted as one stock.

Two days later, a wettable powder containing each of the active compounds of this invention shown in Table 3 was weighed to a predetermined amount, diluted with 10 ml of water, and applied to the irrigated water surface in each pot. Then, the treated pots were allowed to stand in a greenhouse, and the control effect and phytotoxicity on rice plants were examined two weeks later.

The evaluation was made on a scale of 10 grades where 0 represents normal growth and 10 represents complete withering.

The results are shown in Table 3.

TABLE 3

| Active compound | Amount of the active compound (g/10 ares) | Phytotoxicity to rice | | Control effect | | | |
|---|---|---|---|---|---|---|---|
| | | Transplantation | Direct sowing | Barnyard grass | Broadleaved weeds | Bulrush | Slender spikerush |
| No. 16 | 1000 | 0 | 3 | 10 | 4 | 6 | 4 |
| | 500 | 0 | 1 | 8 | 3 | 1 | 1 |
| | 250 | 0 | 0 | 7 | 1 | 0 | 0 |
| | 125 | 0 | 0 | 1 | 0 | 0 | 0 |
| No. 17 | 1000 | 0 | 0 | 6 | 3 | 4 | 0 |
| | 500 | 0 | 0 | 4 | 1 | 2 | 0 |
| | 250 | 0 | 0 | 2 | 0 | 0 | 0 |
| | 125 | 0 | 0 | 1 | 0 | 0 | 0 |
| No. 18 | 1000 | 0 | 2 | 10 | 5 | 7 | 3 |
| | 500 | 0 | 0 | 7 | 4 | 5 | 0 |
| | 250 | 0 | 0 | 1 | 0 | 3 | 0 |
| | 125 | 0 | 0 | 0 | 0 | 0 | 0 |
| No. 19 | 1000 | 0 | 0 | 10 | 6 | 6 | 3 |
| | 500 | 0 | 0 | 8 | 4 | 4 | 0 |
| | 250 | 0 | 0 | 3 | 3 | 2 | 0 |
| | 125 | 0 | 0 | 2 | 0 | 0 | 0 |
| No. 20 | 1000 | 0 | 0 | 6 | 3 | 4 | 0 |
| | 500 | 0 | 0 | 3 | 2 | 2 | 0 |
| | 250 | 0 | 0 | 2 | 0 | 0 | 0 |
| | 125 | 0 | 0 | 0 | 0 | 0 | 0 |
| No. 21 | 1000 | 0 | 2 | 10 | 2 | 6 | 4 |
| | 500 | 0 | 0 | 7 | 2 | 4 | 1 |
| | 250 | 0 | 0 | 3 | 1 | 1 | 0 |
| | 125 | 0 | 0 | 1 | 0 | 0 | 0 |
| No. 22 | 1000 | 0 | 3 | 10 | 4 | 7 | 3 |
| | 500 | 0 | 1 | 5 | 3 | 3 | 1 |
| | 250 | 0 | 0 | 4 | 1 | 2 | 0 |
| | 125 | 0 | 0 | 2 | 0 | 1 | 0 |
| No. 23 | 1000 | 0 | 2 | 10 | 3 | 6 | 3 |
| | 500 | 0 | 1 | 6 | 2 | 3 | 1 |
| | 250 | 0 | 0 | 2 | 1 | 0 | 0 |
| | 125 | 0 | 0 | 1 | 0 | 0 | 0 |
| No. 24 | 1000 | 0 | 2 | 10 | 4 | 0 | 4 |
| | 500 | 0 | 1 | 6 | 1 | 0 | 1 |
| | 250 | 0 | 0 | 3 | 0 | 0 | 0 |
| | 125 | 0 | 0 | 1 | 0 | 0 | 0 |
| No. 25 | 1000 | 0 | 0 | 6 | 3 | 3 | 2 |
| | 500 | 0 | 0 | 3 | 1 | 1 | 0 |
| | 250 | 0 | 0 | 1 | 0 | 0 | 0 |
| | 125 | 0 | 0 | 0 | 0 | 0 | 0 |
| No. 26 | 1000 | 0 | 0 | 7 | 3 | 4 | 0 |
| | 500 | 0 | 0 | 4 | 2 | 2 | 0 |
| | 250 | 0 | 0 | 2 | 0 | 0 | 0 |
| | 125 | 0 | 0 | 0 | 0 | 0 | 0 |
| No. 27 | 1000 | 0 | 0 | 10 | 8 | 10 | 6 |
| | 500 | 0 | 0 | 10 | 3 | 10 | 3 |
| | 250 | 0 | 0 | 10 | 0 | 10 | 0 |
| | 125 | 0 | 0 | 10 | 0 | 10 | 0 |
| No. 28 | 1000 | 0 | 0 | 10 | 7 | 10 | 4 |
| | 500 | 0 | 0 | 10 | 4 | 10 | 2 |
| | 250 | 0 | 0 | 10 | 1 | 10 | 0 |
| | 125 | 0 | 0 | 10 | 0 | 10 | 0 |
| No. 29 | 1000 | 0 | 5 | 10 | 2 | 10 | 2 |
| | 500 | 0 | 0 | 10 | 1 | 10 | 0 |
| | 250 | 0 | 0 | 8 | 0 | 8 | 0 |
| | 125 | 0 | 0 | 4 | 0 | 2 | 0 |
| No. 30 | 1000 | 0 | 0 | 10 | 3 | 10 | 3 |
| | 500 | 0 | 0 | 10 | 1 | 10 | 1 |
| | 250 | 0 | 0 | 9 | 0 | 6 | 0 |
| | 125 | 0 | 0 | 1 | 0 | 0 | 0 |
| No. 31 | 1000 | 0 | 0 | 10 | 5 | 10 | 5 |
| | 500 | 0 | 0 | 10 | 2 | 10 | 2 |
| | 250 | 0 | 0 | 5 | 0 | 4 | 0 |
| | 125 | 0 | 0 | 4 | 0 | 1 | 0 |
| No. 32 | 1000 | 0 | 0 | 10 | 6 | 10 | 6 |
| | 500 | 0 | 0 | 10 | 3 | 9 | 1 |
| | 250 | 0 | 0 | 9 | 0 | 6 | 0 |
| | 125 | 0 | 0 | 8 | 0 | 1 | 0 |

TABLE 3-continued

| Active compound | Amount of the active compound (g/10 ares) | Phytotoxicity to rice | | Control effect | | | |
|---|---|---|---|---|---|---|---|
| | | Trans-plant-ation | Direct sowing | Barn-yard grass | Broad-leaved weeds | Bulrush | Slender spikerush |
| No. 33 | 1000 | 0 | 0 | 10 | 2 | 10 | 2 |
| | 500 | 0 | 0 | 9 | 0 | 8 | 0 |
| | 250 | 0 | 0 | 9 | 0 | 6 | 0 |
| | 125 | 0 | 0 | 8 | 0 | 4 | 0 |
| No. 34 | 1000 | 0 | 3 | 8 | 0 | 6 | 0 |
| | 500 | 0 | 0 | 7 | 0 | 4 | 0 |
| | 250 | 0 | 0 | 6 | 0 | 3 | 0 |
| | 125 | 0 | 0 | 3 | 0 | 0 | 0 |
| No. 35 | 1000 | 0 | 0 | 10 | 3 | 10 | 2 |
| | 500 | 0 | 0 | 10 | 1 | 10 | 0 |
| | 250 | 0 | 0 | 8 | 0 | 8 | 0 |
| | 125 | 0 | 0 | 4 | 0 | 2 | 0 |
| No. 36 | 1000 | 0 | 0 | 10 | 10 | 10 | 8 |
| | 500 | 0 | 0 | 10 | 9 | 10 | 6 |
| | 250 | 0 | 0 | 6 | 0 | 8 | 0 |
| | 125 | 0 | 0 | 0 | 0 | 0 | 0 |
| No. 37 | 1000 | 0 | 0 | 8 | 8 | 8 | 0 |
| | 500 | 0 | 0 | 6 | 6 | 4 | 0 |
| | 250 | 0 | 0 | 0 | 0 | 0 | 0 |
| | 125 | 0 | 0 | 0 | 0 | 0 | 0 |
| No. 38 | 1000 | 0 | 0 | 10 | 10 | 10 | 7 |
| | 500 | 0 | 0 | 10 | 8 | 10 | 4 |
| | 250 | 0 | 0 | 10 | 7 | 10 | 1 |
| | 125 | 0 | 0 | 10 | 0 | 10 | 0 |
| No. 39 | 1000 | 0 | 5 | 10 | 6 | 5 | 0 |
| | 500 | 0 | 3 | 9 | 4 | 4 | 0 |
| | 250 | 0 | 1 | 8 | 0 | 0 | 0 |
| | 125 | 0 | 0 | 6 | 0 | 0 | 0 |
| No. 40 | 1000 | 0 | 4 | 10 | 0 | 6 | 0 |
| | 500 | 0 | 1 | 9 | 0 | 4 | 0 |
| | 250 | 0 | 0 | 9 | 0 | 2 | 0 |
| | 125 | 0 | 0 | 8 | 0 | 0 | 0 |
| No. 41 | 1000 | 0 | 2 | 10 | 3 | 6 | 3 |
| | 500 | 0 | 0 | 10 | 1 | 5 | 1 |
| | 250 | 0 | 0 | 8 | 0 | 1 | 0 |
| | 125 | 0 | 0 | 6 | 0 | 0 | 0 |
| No. 42 | 1000 | 0 | 0 | 10 | 6 | 9 | 3 |
| | 500 | 0 | 0 | 10 | 4 | 6 | 0 |
| | 250 | 0 | 0 | 4 | 0 | 2 | 0 |
| | 125 | 0 | 0 | 2 | 0 | 0 | 0 |
| No. 43 | 1000 | 0 | 0 | 8 | 0 | 4 | 0 |
| | 500 | 0 | 0 | 6 | 0 | 1 | 0 |
| | 250 | 0 | 0 | 2 | 0 | 0 | 0 |
| | 125 | 0 | 0 | 0 | 0 | 0 | 0 |
| No. 44 | 1000 | 0 | 0 | 10 | 4 | 10 | 0 |
| | 500 | 0 | 0 | 10 | 0 | 8 | 0 |
| | 250 | 0 | 0 | 9 | 0 | 4 | 0 |
| | 125 | 0 | 0 | 8 | 0 | 1 | 0 |
| No. 45 | 1000 | 0 | 3 | 10 | 5 | 6 | 5 |
| | 500 | 0 | 0 | 10 | 2 | 4 | 3 |
| | 250 | 0 | 0 | 10 | 0 | 3 | 0 |
| | 125 | 0 | 0 | 8 | 0 | 2 | 0 |
| No. 46 | 1000 | 0 | 0 | 10 | 10 | 7 | 0 |
| | 500 | 0 | 0 | 9 | 6 | 4 | 0 |
| | 250 | 0 | 0 | 7 | 6 | 1 | 0 |
| | 125 | 0 | 0 | 4 | 4 | 1 | 0 |
| No. 47 | 1000 | 0 | 6 | 10 | 4 | 10 | 3 |
| | 500 | 0 | 4 | 10 | 0 | 7 | 1 |
| | 250 | 0 | 2 | 6 | 0 | 4 | 0 |
| | 125 | 0 | 0 | 2 | 0 | 2 | 0 |
| No. 48 | 1000 | 0 | 0 | 10 | 0 | 10 | 8 |
| | 500 | 0 | 0 | 10 | 0 | 10 | 4 |
| | 250 | 0 | 0 | 10 | 0 | 9 | 0 |
| | 125 | 0 | 0 | 9 | 0 | 8 | 0 |
| No. 49 | 1000 | 0 | 0 | 10 | 8 | 5 | 0 |
| | 500 | 0 | 0 | 10 | 8 | 4 | 0 |
| | 250 | 0 | 0 | 9 | 0 | 2 | 0 |
| | 125 | 0 | 0 | 4 | 0 | 0 | 0 |
| No. 50 | 1000 | 0 | 0 | 10 | 8 | 10 | 5 |
| | 500 | 0 | 0 | 10 | 7 | 10 | 4 |
| | 250 | 0 | 0 | 10 | 4 | 10 | 1 |
| | 125 | 0 | 0 | 10 | 0 | 8 | 0 |
| No. 51 | 1000 | 0 | 0 | 9 | 6 | 3 | 6 |
| | 500 | 0 | 0 | 4 | 4 | 1 | 0 |
| | 250 | 0 | 0 | 2 | 2 | 0 | 0 |
| | 125 | 0 | 0 | 1 | 0 | 0 | 0 |
| No. 52 | 1000 | 0 | 0 | 9 | 4 | 2 | 0 |

TABLE 3-continued

| Active compound | Amount of the active compound (g/10 ares) | Phytotoxicity to rice Transplantation | Phytotoxicity to rice Direct sowing | Control effect Barnyard grass | Control effect Broad-leaved weeds | Control effect Bulrush | Control effect Slender spikerush |
|---|---|---|---|---|---|---|---|
| | 500 | 0 | 0 | 5 | 1 | 1 | 0 |
| | 250 | 0 | 0 | 3 | 0 | 0 | 0 |
| | 125 | 0 | 0 | 0 | 0 | 0 | 0 |
| No. 53 | 1000 | 0 | 0 | 10 | 3 | 3 | 3 |
| | 500 | 0 | 0 | 6 | 1 | 0 | 0 |
| | 250 | 0 | 0 | 3 | 0 | 0 | 0 |
| | 125 | 0 | 0 | 0 | 0 | 0 | 0 |
| No. 54 | 1000 | 0 | 0 | 9 | 2 | 4 | 0 |
| | 500 | 0 | 0 | 6 | 1 | 2 | 0 |
| | 250 | 0 | 0 | 3 | 0 | 0 | 0 |
| | 125 | 0 | 0 | 0 | 0 | 0 | 0 |
| No. 55 | 1000 | 0 | 0 | 8 | 4 | 1 | 2 |
| | 500 | 0 | 0 | 2 | 1 | 0 | 0 |
| | 250 | 0 | 0 | 0 | 0 | 0 | 0 |
| | 125 | 0 | 0 | 0 | 0 | 0 | 0 |
| No. 56 | 1000 | 0 | 0 | 7 | 2 | 4 | 0 |
| | 500 | 0 | 0 | 3 | 1 | 0 | 0 |
| | 250 | 0 | 0 | 1 | 0 | 0 | 0 |
| | 125 | 0 | 0 | 0 | 0 | 0 | 0 |
| No. 57 | 1000 | 0 | 0 | 6 | 3 | 0 | 3 |
| | 500 | 0 | 0 | 2 | 2 | 0 | 1 |
| | 250 | 0 | 0 | 1 | 0 | 0 | 0 |
| | 125 | 0 | 0 | 0 | 0 | 0 | 0 |
| No. 58 | 1000 | 0 | 0 | 6 | 0 | 0 | 0 |
| | 500 | 0 | 0 | 4 | 0 | 0 | 0 |
| | 250 | 0 | 0 | 2 | 0 | 0 | 0 |
| | 125 | 0 | 0 | 0 | 0 | 0 | 0 |
| No. 59 | 1000 | 0 | 0 | 7 | 0 | 0 | 0 |
| | 500 | 0 | 0 | 5 | 0 | 0 | 0 |
| | 250 | 0 | 0 | 3 | 0 | 0 | 0 |
| | 125 | 0 | 0 | 0 | 0 | 0 | 0 |
| No. 60 | 1000 | 0 | 0 | 4 | 2 | 1 | 0 |
| | 500 | 0 | 0 | 2 | 0 | 0 | 0 |
| | 250 | 0 | 0 | 0 | 0 | 0 | 0 |
| | 125 | 0 | 0 | 0 | 0 | 0 | 0 |
| No. 61 | 1000 | 0 | 0 | 5 | 0 | 1 | 0 |
| | 500 | 0 | 0 | 2 | 0 | 0 | 0 |
| | 250 | 0 | 0 | 0 | 0 | 0 | 0 |
| | 125 | 0 | 0 | 0 | 0 | 0 | 0 |
| No. 62 | 1000 | 0 | 0 | 10 | 1 | 4 | 4 |
| | 500 | 0 | 0 | 3 | 0 | 1 | 0 |
| | 250 | 0 | 0 | 0 | 0 | 0 | 0 |
| | 125 | 0 | 0 | 0 | 0 | 0 | 0 |
| No. 63 | 1000 | 0 | 3 | 10 | 10 | 10 | 7 |
| | 500 | 0 | 1 | 10 | 10 | 10 | 3 |
| | 250 | 0 | 0 | 10 | 6 | 8 | 1 |
| | 125 | 0 | 0 | 10 | 4 | 3 | 0 |
| Known compound A* | 1000 | 0 | 0 | 1 | 0 | 1 | 0 |
| | 500 | 0 | 0 | 0 | 0 | 0 | 0 |
| | 250 | 0 | 0 | 0 | 0 | 0 | 0 |
| | 125 | 0 | 0 | 0 | 0 | 0 | 0 |
| Known compound B** | 1000 | 0 | 0 | 1 | 0 | 1 | 0 |
| | 500 | 0 | 0 | 0 | 0 | 0 | 0 |
| | 250 | 0 | 0 | 0 | 0 | 0 | 0 |
| | 125 | 0 | 0 | 0 | 0 | 0 | 0 |
| Benthiocarb (control) | 500 | 6 | 10 | 10 | 10 | 10 | 10 |
| | 250 | 2 | 10 | 10 | 7 | 4 | 10 |
| | 125 | 0 | 10 | 10 | 4 | 1 | 6 |
| | 62.5 | 0 | 8 | 8 | 0 | 0 | 1 |
| CNP (control) | 500 | 7 | 10 | 10 | 10 | 4 | 6 |
| | 250 | 2 | 10 | 10 | 9 | 1 | 1 |
| | 125 | 0 | 10 | 9 | 4 | 0 | 0 |
| | 62.5 | 0 | 10 | 6 | 1 | 0 | 0 |
| Untreated | — | 0 | 0 | 0 | 0 | 0 | 0 |

*Known compound A: N-methyl-N-benzyl-2-nitrobenzenesulfonamide
**Known compound B: N-2-bromoethyl-N-benzoyl-4-methylbenzenesulfonamide

EXAMPLE E

Two sheets of filter paper were spread in a Petri dish with a diameter of 9 cm, and 6 ml of a wettable powder of each of the active compounds of this invention shown in Table 4 in a predetermined concentration was dropped onto them. Ten seeds each of barnyard grass and rice plant (variety: Nihonbare) were directly sown. The Petri dish was put into a thermostat chamber at 26° C., and 72 hours later, the lengths of young stems and leaves and young roots were measured.

The evaluation was made on a scale of 10 grades in which 10 represents complete inhibition and 0 represents normal growth.

TABLE 4

| Active compound No. | Concentration (ppm) | Barnyard grass Young stem | Barnyard grass Root | Rice plant Young stem | Rice plant Root |
|---|---|---|---|---|---|
|  | 1,000 | 7 | 9 | 0 | 0 |
|  | 300 | 5 | 7 | 0 | 0 |
| 64 | 100 | 4 | 7 | 0 | 0 |
|  | 30 | 2 | 3 | 0 | 0 |
|  | 10 | 1 | 2 | 0 | 0 |
|  | 1,000 | 10 | 9 | 0 | 0 |
|  | 300 | 7 | 8 | 0 | 0 |
| 65 | 100 | 4 | 5 | 0 | 0 |
|  | 30 | 3 | 5 | 0 | 0 |
|  | 10 | 1 | 2 | 0 | 0 |
|  | 1,000 | 9 | 10 | 0 | 0 |
|  | 300 | 9 | 9 | 0 | 0 |
| 66 | 100 | 7 | 5 | 0 | 0 |
|  | 30 | 2 | 3 | 0 | 0 |
|  | 10 | 1 | 1 | 0 | 0 |
|  | 1,000 | 10 | 10 | 3 | 2 |
|  | 300 | 10 | 10 | 1 | 0 |
| 67 | 100 | 10 | 10 | 0 | 0 |
|  | 30 | 8 | 7 | 0 | 0 |
|  | 10 | 5 | 4 | 0 | 0 |
|  | 1,000 | 10 | 10 | 0 | 0 |
|  | 300 | 9 | 10 | 0 | 0 |
| 68 | 100 | 5 | 8 | 0 | 0 |
|  | 30 | 3 | 6 | 0 | 0 |
|  | 10 | 2 | 3 | 0 | 0 |
|  | 1,000 | 7 | 10 | 0 | 0 |
|  | 300 | 5 | 7 | 0 | 0 |
| 69 | 100 | 3 | 6 | 0 | 0 |
|  | 30 | 1 | 3 | 0 | 0 |
|  | 10 | 0 | 1 | 0 | 0 |
|  | 1,000 | 10 | 10 | 3 | 1 |
|  | 300 | 8 | 10 | 0 | 0 |
| 70 | 100 | 5 | 7 | 0 | 0 |
|  | 30 | 2 | 2 | 0 | 0 |
|  | 10 | 1 | 1 | 0 | 0 |
|  | 1,000 | 7 | 6 | 0 | 0 |
|  | 300 | 6 | 6 | 0 | 0 |
| 71 | 100 | 3 | 5 | 0 | 0 |
|  | 30 | 1 | 2 | 0 | 0 |
|  | 10 | 0 | 0 | 0 | 0 |
|  | 1,000 | 6 | 8 | 0 | 0 |
|  | 300 | 4 | 3 | 0 | 0 |
| 72 | 100 | 2 | 1 | 0 | 0 |
|  | 30 | 0 | 0 | 0 | 0 |
|  | 10 | 0 | 0 | 0 | 0 |
|  | 1,000 | 8 | 10 | 0 | 0 |
|  | 300 | 6 | 9 | 0 | 0 |
| 73 | 100 | 4 | 5 | 0 | 0 |
|  | 30 | 1 | 3 | 0 | 0 |
|  | 10 | 0 | 0 | 0 | 0 |
|  | 1,000 | 10 | 10 | 4 | 1 |
|  | 300 | 9 | 10 | 2 | 0 |
| 74 | 100 | 7 | 9 | 0 | 0 |
|  | 30 | 3 | 4 | 0 | 0 |
|  | 10 | 1 | 2 | 0 | 0 |
|  | 1,000 | 10 | 10 | 5 | 4 |
|  | 300 | 10 | 10 | 2 | 1 |
| 75 | 100 | 10 | 10 | 0 | 0 |
|  | 30 | 9 | 10 | 0 | 0 |
|  | 10 | 9 | 7 | 0 | 0 |
|  | 1,000 | 10 | 10 | 7 | 6 |
|  | 300 | 10 | 10 | 3 | 2 |
| 76 | 100 | 10 | 10 | 0 | 0 |
|  | 30 | 9 | 9 | 0 | 0 |
|  | 10 | 9 | 9 | 0 | 0 |
|  | 1,000 | 10 | 10 | 5 | 2 |
|  | 300 | 10 | 10 | 4 | 1 |
| 77 | 100 | 10 | 10 | 1 | 0 |
|  | 30 | 9 | 9 | 0 | 0 |
|  | 10 | 8 | 7 | 0 | 0 |
|  | 1,000 | 10 | 10 | 7 | 3 |
|  | 300 | 10 | 10 | 4 | 1 |
| 78 | 100 | 8 | 9 | 0 | 0 |
|  | 30 | 7 | 6 | 0 | 0 |
|  | 10 | 6 | 3 | 0 | 0 |
|  | 1,000 | 10 | 10 | 7 | 6 |
|  | 300 | 10 | 10 | 5 | 3 |
| 79 | 100 | 9 | 8 | 1 | 0 |
|  | 30 | 7 | 5 | 0 | 0 |
|  | 10 | 3 | 3 | 0 | 0 |
|  | 1,000 | 10 | 10 | 6 | 3 |
|  | 300 | 10 | 9 | 4 | 2 |
| 80 | 100 | 10 | 6 | 0 | 0 |
|  | 30 | 7 | 2 | 0 | 0 |
|  | 10 | 2 | 1 | 0 | 0 |
|  | 1,000 | 10 | 10 | 8 | 5 |
|  | 300 | 10 | 10 | 2 | 2 |
| 81 | 100 | 10 | 6 | 0 | 0 |
|  | 30 | 6 | 2 | 0 | 0 |
|  | 10 | 3 | 1 | 0 | 0 |
|  | 1,000 | 8 | 10 | 0 | 0 |
|  | 300 | 4 | 7 | 0 | 0 |
| 82 | 100 | 2 | 6 | 0 | 0 |
|  | 30 | 1 | 3 | 0 | 0 |
|  | 10 | 0 | 1 | 0 | 0 |
|  | 1,000 | 8 | 10 | 1/ 0 |  |
|  | 300 | 7 | 9 | 0 | 0 |
| 83 | 100 | 5 | 3 | 0 | 0 |
|  | 30 | 4 | 0 | 0 | 0 |
|  | 10 | 0 | 0 | 0 | 0 |
|  | 1,000 | 8 | 10 | 0 | 0 |
|  | 300 | 7 | 9 | 0 | 0 |
| 84 | 100 | 6 | 4 | 0 | 0 |
|  | 30 | 3 | 1 | 0 | 0 |
|  | 10 | 1 | 0 | 0 | 0 |
|  | 1,000 | 10 | 10 | 6 | 7 |
|  | 300 | 10 | 10 | 0 | 0 |
| 85 | 100 | 10 | 10 | 0 | 0 |
|  | 30 | 9 | 10 | 0 | 0 |
|  | 10 | 9 | 9 | 0 | 0 |
|  | 1,000 | 10 | 10 | 7 | 4 |
|  | 300 | 10 | 3 | 0 | 0 |
| 86 | 100 | 8 | 0 | 0 | 0 |
|  | 30 | 6 | 0 | 0 | 0 |
|  | 10 | 1 | 0 | 0 | 0 |
|  | 1,000 | 5 | 10 | 8 | 9 |
|  | 300 | 9 | 7 | 0 | 1 |
| 87 | 100 | 8 | 3 | 0 | 0 |
|  | 30 | 4 | 2 | 0 | 0 |
|  | 10 | 1 | 1 | 0 | 0 |
|  | 1,000 | 10 | 10 | 5 | 1 |
|  | 300 | 10 | 3 | 2 | 1 |
| 88 | 100 | 8 | 2 | 0 | 0 |
|  | 30 | 6 | 0 | 0 | 0 |
|  | 10 | 2 | 0 | 0 | 0 |
|  | 1,000 | 10 | 10 | 8 | 9 |
|  | 300 | 10 | 2 | 7 | 3 |
| 89 | 100 | 10 | 0 | 5 | 1 |
|  | 30 | 10 | 0 | 0 | 0 |
|  | 10 | 7 | 0 | 0 | 0 |
|  | 1,000 | 10 | 10 | 10 | 10 |
|  | 300 | 10 | 10 | 6 | 4 |
| 90 | 100 | 10 | 4 | 6 | 0 |
|  | 30 | 10 | 0 | 2 | 0 |
|  | 10 | 9 | 0 | 1 | 0 |
|  | 1,000 | 10 | 10 | 10 | 10 |
|  | 300 | 10 | 8 | 8 | 4 |
| 91 | 100 | 10 | 3 | 7 | 0 |
|  | 30 | 10 | 0 | 1 | 0 |
|  | 10 | 9 | 0 | 0 | 0 |
|  | 1,000 | 10 | 10 | 9 | 9 |
|  | 300 | 10 | 3 | 5 | 2 |
| 92 | 100 | 10 | 0 | 0 | 0 |
|  | 30 | 6 | 0 | 0 | 0 |
|  | 10 | 2 | 0 | 0 | 0 |
|  | 1,000 | 10 | 10 | 10 | 10 |
|  | 300 | 10 | 9 | 5 | 1 |
| 93 | 100 | 10 | 7 | 1 | 0 |
|  | 30 | 7 | 6 | 0 | 0 |
|  | 10 | 4 | 1 | 0 | 0 |
|  | 1,000 | 10 | 10 | 9 | 9 |
|  | 300 | 10 | 7 | 6 | 1 |
| 94 | 100 | 7 | 4 | 2 | 0 |
|  | 30 | 6 | 1 | 0 | 0 |
|  | 10 | 4 | 0 | 0 | 0 |
|  | 1,000 | 10 | 10 | 8 | 7 |

TABLE 4-continued

| Active compound No. | Concent-ration (ppm) | Barnyard grass Young stem | Root | Rice plant Young stem | Root |
|---|---|---|---|---|---|
| 95 | 300 | 10 | 10 | 1 | 3 |
|  | 100 | 10 | 10 | 0 | 0 |
|  | 30 | 9 | 6 | 0 | 0 |
|  | 10 | 4 | 2 | 0 | 0 |
| 96 | 1,000 | 10 | 10 | 7 | 5 |
|  | 300 | 10 | 10 | 4 | 2 |
|  | 100 | 10 | 7 | 1 | 0 |
|  | 30 | 7 | 4 | 0 | 0 |
|  | 10 | 4 | 0 | 0 | 0 |
| 97 | 1,000 | 10 | 10 | 10 | 10 |
|  | 300 | 10 | 9 | 10 | 9 |
|  | 100 | 10 | 4 | 10 | 6 |
|  | 30 | 6 | 1 | 7 | 2 |
|  | 10 | 2 | 0 | 3 | 0 |
| 98 | 1,000 | 10 | 10 | 8 | 8 |
|  | 300 | 10 | 9 | 6 | 4 |
|  | 100 | 9 | 8 | 4 | 2 |
|  | 30 | 7 | 6 | 2 | 0 |
|  | 10 | 4 | 2 | 0 | 0 |
| 99 | 1,000 | 10 | 10 | 7 | 6 |
|  | 300 | 10 | 10 | 6 | 4 |
|  | 100 | 9 | 9 | 2 | 1 |
|  | 30 | 8 | 7 | 0 | 0 |
|  | 10 | 7 | 6 | 0 | 0 |
| 100 | 1,000 | 10 | 10 | 7 | 6 |
|  | 300 | 9 | 9 | 5 | 3 |
|  | 100 | 8 | 8 | 1 | 1 |
|  | 30 | 7 | 6 | 0 | 0 |
|  | 10 | 6 | 4 | 0 | 0 |
| 101 | 1,000 | 10 | 10 | 4 | 3 |
|  | 300 | 5 | 4 | 1 | 1 |
|  | 100 | 4 | 2 | 0 | 0 |
|  | 30 | 1 | 0 | 0 | 0 |
|  | 10 | 0 | 0 | 0 | 0 |
| 102 | 1,000 | 10 | 10 | 5 | 2 |
|  | 300 | 6 | 5 | 2 | 1 |
|  | 100 | 5 | 4 | 0 | 0 |
|  | 30 | 2 | 1 | 0 | 0 |
|  | 10 | 0 | 0 | 0 | 0 |
| Benthio-carb (control) | 1,000 | 10 | 10 | 10 | 10 |
|  | 300 | 10 | 9 | 10 | 9 |
|  | 100 | 10 | 4 | 10 | 6 |
|  | 30 | 6 | 1 | 7 | 2 |
|  | 10 | 2 | 0 | 3 | 0 |
| Untreated | — | 0 | 0 | 0 | 0 |

EXAMPLE F

A paddy soil was put into pots (1/5000 are), and the surface soil to a depth of 1 cm and 30 seeds of barnyard grass were mixed. Ten seeds of rice (variety: Nihonbare) were sown on the surface of the soil, and two seedlings of rice each in the 1-leaf stage, 2-leaf stage, and 3.5-leaf stage respectively were transplanted as one stock. The pots were irrigated to a water depth of 2 cm. One day later, a predetermined amount of each of the active compounds of this invention indicated in Table 5 was diluted with 10 ml of water, and dropped onto the soil surface in each pot. The control effect and phytotoxicity were examined in the same manner as in Example D 20 days after the treatment. The results are shown in Table 5.

TABLE 5

| Active compound | Amount of the active compound (g/10 ares) | Control effect on barnyard grass | Phytotoxicity to rice Directly sown | 1-leaf stage | 2-leaf stage | 3,5-leaf stage |
|---|---|---|---|---|---|---|
| No. 27 | 1000 | 10 | 0 | 0 | 0 | 0 |
|  | 500 | 10 | 0 | 0 | 0 | 0 |
|  | 250 | 10 | 0 | 0 | 0 | 0 |
|  | 125 | 10 | 0 | 0 | 0 | 0 |
|  | 62.5 | 10 | 0 | 0 | 0 | 0 |
| No. 28 | 1000 | 10 | 0 | 0 | 0 | 0 |
|  | 500 | 10 | 0 | 0 | 0 | 0 |
|  | 250 | 10 | 0 | 0 | 0 | 0 |
|  | 125 | 10 | 0 | 0 | 0 | 0 |
|  | 62.5 | 10 | 0 | 0 | 0 | 0 |
| No. 67 | 1000 | 10 | 0 | 0 | 0 | 0 |
|  | 500 | 10 | 0 | 0 | 0 | 0 |
|  | 250 | 10 | 0 | 0 | 0 | 0 |
|  | 125 | 10 | 0 | 0 | 0 | 0 |
|  | 62.5 | 7 | 0 | 0 | 0 | 0 |
| No. 85 | 1000 | 10 | 0 | 0 | 0 | 0 |
|  | 500 | 10 | 0 | 0 | 0 | 0 |
|  | 250 | 10 | 0 | 0 | 0 | 0 |
|  | 125 | 9 | 0 | 0 | 0 | 0 |
|  | 62.5 | 8 | 0 | 0 | 0 | 0 |
| Benthio-carb (control) | 1000 | 10 | 10 | 10 | 9 | 7 |
|  | 500 | 10 | 10 | 10 | 6 | 3 |
|  | 250 | 10 | 10 | 5 | 1 | 0 |
|  | 125 | 10 | 10 | 2 | 0 | 0 |
|  | 62.5 | 9 | 8 | 0 | 0 | 0 |
| CNP (control) | 1000 | 10 | 10 | 10 | 10 | 9 |
|  | 500 | 10 | 10 | 8 | 7 | 4 |
|  | 250 | 10 | 10 | 7 | 4 | 1 |
|  | 125 | 10 | 10 | 5 | 2 | 0 |
|  | 62.5 | 7 | 7 | 3 | 0 | 0 |
| Untreated | — | 0 | 0 | 0 | 0 | 0 |

EXAMPLE G

A test on an enlarged scale was conducted under assumed field conditions.

Paddy soil was put into a concrete pot having a length of 70 cm, a width of 70 cm and a height of 50 cm and rendered muddy. Sixty seeds of barnyard grass (Echinochloa crus-galli Beauv.) were sown, and the pot was irrigated to a water depth of 3 cm. Further, 20 germinated seeds of rice (variety: Nihonbare) were sown on the soil. Three-leaf stage rice seedlings of the same variety of rice were planted in four stocks each consisting of two seedlings. One day later, a granule of each of the active compounds of this invention shown in Table 6 and Benthiocarb as a control was sprayed by hand in each of the amounts indicated in Table 6. The control effect (broad-leaved grasses were those which occurred naturally) and phytotoxicity to rice were examined two weeks after the treatment. The results are shown in Table 6.

TABLE 6

| Active compound | Amount of the active compound (g/10 ares) | Phytotoxicity to rice Direct sowing | Trans-plantation | Control effect Barnyard grass | Broad-leaved weeds |
|---|---|---|---|---|---|
| No. 27 | 1000 | 0 | 0 | 10 | 2 |
|  | 500 | 0 | 0 | 10 | 0 |
|  | 250 | 0 | 0 | 10 | 0 |
|  | 125 | 0 | 0 | 7 | 0 |
| No. 28 | 1000 | 0 | 0 | 10 | 0 |
|  | 500 | 0 | 0 | 10 | 0 |
|  | 250 | 0 | 0 | 10 | 0 |
|  | 125 | 0 | 0 | 6 | 0 |
| No. 31 | 1000 | 0 | 0 | 10 | 0 |
|  | 500 | 0 | 0 | 10 | 0 |
|  | 250 | 0 | 0 | 8 | 0 |
|  | 125 | 0 | 0 | 6 | 0 |
| No. 32 | 1000 | 0 | 0 | 10 | 0 |
|  | 500 | 0 | 0 | 10 | 0 |
|  | 250 | 0 | 0 | 6 | 0 |

TABLE 6-continued

| Active compound | Amount of the active compound (g/10 ares) | Phytotoxicity to rice | | Control effect | |
|---|---|---|---|---|---|
| | | Direct sowing | Trans- plantation | Barnyard grass | Broad- leaved weeds |
| | 125 | 0 | 0 | 3 | 0 |
| No. 33 | 1000 | 0 | 0 | 10 | 0 |
| | 500 | 0 | 0 | 8 | 0 |
| | 250 | 0 | 0 | 5 | 0 |
| | 125 | 0 | 0 | 4 | 0 |
| No. 67 | 1000 | 0 | 0 | 10 | 0 |
| | 500 | 0 | 0 | 10 | 0 |
| | 250 | 0 | 0 | 10 | 0 |
| | 125 | 0 | 0 | 8 | 0 |
| No. 85 | 1000 | 0 | 0 | 10 | 0 |
| | 500 | 0 | 0 | 10 | 0 |
| | 250 | 0 | 0 | 7 | 0 |
| | 125 | 0 | 0 | 5 | 0 |
| Benthio- carb (control) | 500 | 10 | 3 | 10 | 8 |
| | 250 | 10 | 1 | 10 | 5 |
| | 125 | 8 | 0 | 9 | 2 |
| | 62.5 | 3 | 0 | 4 | 1 |
| Untreated | — | 0 | 0 | 0 | 0 |

EXAMPLE H

Silt loam (a clay content of 48.5%) and sandy soil (a clay content of 15.4%) were each placed in pots (1/5000 are), and agitated until a paddy field condition was attained. Thirty seeds of barnyard grass (*Echinochloa crus-galli* Beauv.) were sown per pot. Further, ten germinated seeds of rice were sown, and rice seedings in the three-leaf stage were planted in two stocks each consisting of two seedlings. The soil surface was submerged to a water depth of 3 cm. One day later, a wettable powder of each of the active compounds of this invention indicated in Table 7 was applied. Two weeks after the treatment, the control effect was examined in the same way as in Example D. The results are shown in Table 7.

TABLE 7

| Active compound | Amount of the active compound (g/10 ares) | Sandy soil | | | Silt loam | | |
|---|---|---|---|---|---|---|---|
| | | Barn- yard grass | Directly sown rice plant | Trans- planted rice plant | Barn- yard grass | Directly sown rice plant | Trans- planted rice plant |
| No. 27 | 500 | 10 | 0 | 0 | 10 | 0 | 0 |
| | 250 | 10 | 0 | 0 | 10 | 0 | 0 |
| | 125 | 10 | 0 | 0 | 10 | 0 | 0 |
| | 62.5 | 10 | 0 | 0 | 10 | 0 | 0 |
| No. 31 | 500 | 10 | 0 | 0 | 100 | 0 | 0 |
| | 250 | 10 | 0 | 0 | 7 | 0 | 0 |
| | 125 | 10 | 0 | 0 | 4 | 0 | 0 |
| | 62.5 | 4 | 0 | 0 | 1 | 0 | 0 |
| No. 32 | 500 | 10 | 0 | 0 | 10 | 0 | 0 |
| | 250 | 10 | 0 | 0 | 9 | 0 | 0 |
| | 125 | 9 | 0 | 0 | 8 | 0 | 0 |
| | 62.5 | 7 | 0 | 0 | 4 | 0 | 0 |
| No. 33 | 500 | 10 | 0 | 0 | 10 | 0 | 0 |
| | 250 | 10 | 0 | 0 | 9 | 0 | 0 |
| | 125 | 8 | 0 | 0 | 7 | 0 | 0 |
| | 62.5 | 6 | 0 | 0 | 4 | 0 | 0 |
| Butachlor (control) | 500 | 10 | 10 | 10 | 10 | 10 | 10 |
| | 250 | 10 | 10 | 10 | 10 | 10 | 6 |
| | 125 | 10 | 10 | 7 | 10 | 10 | 3 |
| | 62.5 | 10 | 10 | 4 | 7 | 8 | 0 |
| Benthio- carb (control) | 500 | 10 | 10 | 10 | 10 | 10 | 4 |
| | 250 | 10 | 10 | 8 | 10 | 10 | 2 |
| | 125 | 10 | 10 | 6 | 10 | 10 | 1 |
| | 62.5 | 10 | 10 | 3 | 9 | 8 | 0 |
| Untreated | — | 0 | 0 | 0 | 0 | 0 | 0 |

EXAMPLE I

Three-leaf stage rice seedlings were machine-transplanted in a paddy field, and four days after, the paddy field was divided into areas of 2 m×2 m by vinyl resin plates. A wettable powder of each of the active compounds of this invention shown in Table 8 in a predetermined amount was diluted with 400 ml of water per area and sprayed onto the entire water surface. The control effect and phytotoxicity to rice were examined three weeks later.

The evaluation of the control effect was made on a scale of 10 grades. The phytotoxicity to rice was evaluated on the following standards:

—: Normal
+: slight injury
++: minor injury
+++: moderate injury

The results are shown in Table 8.

TABLE 8

| Active compound | Amount of the active compound (g/10 ares) | Control effect | | | | Toxi- city to rice plants |
|---|---|---|---|---|---|---|
| | | Barn- yard grass | Bul- rush | Um- brella plant | Broad- leaved weeds | |
| No. 27 | 1000 | 10 | 8 | 10 | 5 | — |
| | 500 | 10 | 6 | 9 | 3 | — |
| | 250 | 7 | 4 | 4 | 1 | — |
| | 125 | 4 | 2 | 3 | 1 | — |
| No. 67 | 1000 | 10 | 7 | 10 | 6 | — |
| | 500 | 9 | 5 | 9 | 4 | — |
| | 250 | 7 | 3 | 6 | 1 | — |
| | 125 | 4 | 1 | 3 | 0 | — |
| No. 85 | 1000 | 10 | 7 | 10 | 8 | — |
| | 500 | 8 | 6 | 9 | 5 | — |
| | 250 | 5 | 4 | 6 | 1 | — |
| | 125 | 3 | 1 | 1 | 0 | — |
| MO (control) | 500 | 10 | 10 | 9 | 10 | ++ |
| | 250 | 8 | 5 | 6 | 4 | + |
| | 125 | 4 | 2 | 2 | 1 | — |
| | 62.5 | 1 | 0 | 1 | 0 | — |

What we claim is:

1. A compound of the formula

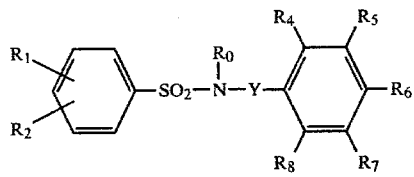

wherein $R_0$ represents alkyl containing up to 15 carbon atoms, alkenyl containing 2 to 4 carbon atoms or propargyl; $R_1$ and $R_2$, independently from each other, represent hydrogen, halogen, alkyl containing 1 to 4 carbon atoms or alkoxy containing 1 to 4 carbon atoms; one or two of $R_4$, $R_5$, $R_6$, $R_7$ and $R_8$ represent hydrogen, halogen, alkyl containing 1 to 4 carbon atoms or alkoxy containing 1 to 4 carbon atoms and the remainder represent hydrogen; and Y represents

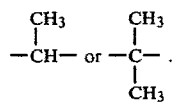

2. The compound of claim 1 wherein $R_0$ is an allyl group.

3. The compound of claim 1 wherein $R_1$ represents hydrogen, halogen, methyl, ethyl, n-propyl or methoxy; $R_2$ is hydrogen; $R_4$ and $R_6$, independently from each other, represent hydrogen, halogen or methyl; and $R_5$, $R_7$ and $R_8$ are all hydrogen.

4. The compound of claim 1 which is a compound of the formula

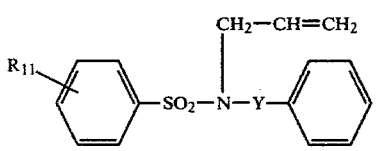

wherein $R_{11}$ represents hydrogen or alkyl containing 1 to 4 carbon atoms, and Y represents

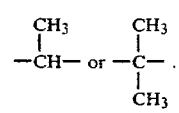

5. The compound of claim 1 wherein $R_0$ is an allyl or propargyl group.

6. The compound of claim 1 wherein $R_4$, $R_5$, $R_6$, $R_7$ and $R_8$ all represent hydrogen atoms.

7. The compound of claim 1 which is a compound of the formula

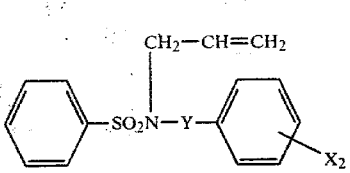

wherein Y is the group

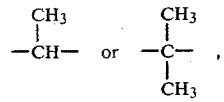

and $X_2$ is a hydrogen or chlorine atom.

8. The compound of claim 1 which is N-allyl-N-($\alpha,\alpha$-dimethylbenzyl)benzenesulfonamide.

9. The compound of claim 1 which is N-allyl-N-($\alpha$-methylbenzyl)benzenesulfonamide.

10. The compound of claim 1 which is N-allyl-N-($\alpha$-methyl-4-chlorobenzyl)benzenesulfonamide.

11. The compound of claim 1 which is N-allyl-N-($\alpha,\alpha$-dimethyl-4-chlorobenzyl)benzenesulfonamide.

12. A herbicidal composition comprising, as an active ingredient, a herbicidally effective amount of a compound of the formula

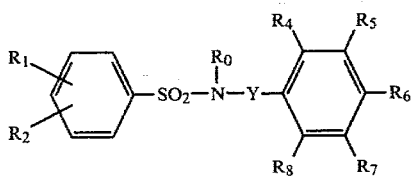

wherein $R_0$ represents alkyl containing up to 15 carbon atoms, alkenyl containing 2 to 4 carbon atoms or propargyl; $R_1$ and $R_2$, independently from each other, represent hydrogen, halogen, alkyl containing 1 to 4 carbon atoms or alkoxy containing 1 to 4 carbon atoms; one or two of $R_4$, $R_5$, $R_6$, $R_7$ and $R_8$ represent hydrogen, halogen, alkyl containing 1 to 4 carbon atoms or alkoxy containing 1 to 4 carbon atoms and the remainder represent hydrogen; and Y represents

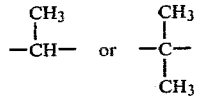

and an inert liquid or solid carrier or diluent.

13. The composition of claim 12 wherein in formula (I), $R_0$ is an allyl or propargyl group.

14. The composition of claim 12 wherein $R_4$, $R_5$, $R_6$, $R_7$ and $R_8$ all represent hydrogen atoms.

15. The composition of claim 12 wherein the active ingredient is a compound of the formula

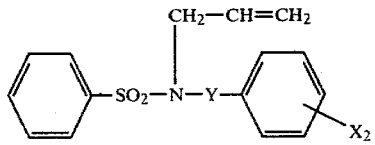

wherein Y is the group

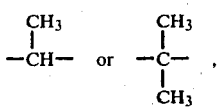

and $X_2$ is a hydrogen or chlorine atom.

16. The composition of claim 12 wherein the amount of the compound of formula (I) is at least 0.5% by weight.

17. The composition of claim 12 wherein the amount of the compound of formula (I) is 1 to 90% by weight.

18. The composition of claim 12 which is in the form of a dust, granules, wettable powder, solution or emulsifiable concentrate.

19. A method for controlling weeds in a rice crop which comprises applying to the locus to be protected from the weeds a herbicidally effective amount of a compound of the formula

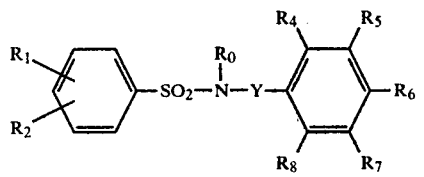

wherein $R_0$ represents alkyl containing up to 15 carbon atoms, alkenyl containing 2 to 4 carbon atoms or propargyl; $R_1$ and $R_2$, independently from each other, represent hydrogen, halogen, alkyl containing 1 to 4 carbon atoms or alkoxy containing 1 to 4 carbon atoms; one or two of $R_4$, $R_5$, $R_6$, $R_7$ and $R_8$ represent hydrogen, halogen, alkyl containing 1 to 4 carbon atoms or alkoxy containing 1 to 4 carbon atoms and the remainder represent hydrogen; and Y represents

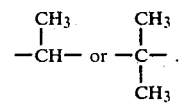

20. The method of claim 19 wherein the compound of formula (I) is applied before or during the germination of the weeds.

21. The method of claim 19 wherein the locus is a paddy field.

22. The method of claim 19 wherein the weed is barnyard grass.

23. The method of claim 19 wherein the amount of the compound of formula (I) applied is at least 25 g/10 ares.

24. The method of claim 19 wherein the amount of the compound of formula (I) applied is 50 to 1000 g/10 ares.

* * * * *